US010519405B2

(12) United States Patent
Andersen et al.

(10) Patent No.: US 10,519,405 B2
(45) Date of Patent: Dec. 31, 2019

(54) STABILIZED ALPHA-AMYLASE VARIANTS AND USE OF THE SAME

(71) Applicant: NOVOZYMES A/S, Bagsvaerd (DK)

(72) Inventors: Carsten Andersen, Vaerloese (DK); Anna-Kathrine Fevre, Holte (DK)

(73) Assignee: NOVOZYMES A/S, Bagsvaerd (DK)

( * ) Notice: Subject to any disclaimer, the term of this patent is extended or adjusted under 35 U.S.C. 154(b) by 0 days.

(21) Appl. No.: 15/481,633

(22) Filed: Apr. 7, 2017

(65) Prior Publication Data
US 2017/0292095 A1 Oct. 12, 2017

(30) Foreign Application Priority Data

Apr. 8, 2016 (DK) .................................. 2016 00210

(51) Int. Cl.
C12N 9/28 (2006.01)
C12N 15/56 (2006.01)
C12N 1/21 (2006.01)
C11D 3/386 (2006.01)
C11D 11/00 (2006.01)
C12N 9/26 (2006.01)

(52) U.S. Cl.
CPC .......... *C11D 3/386* (2013.01); *C11D 3/38609* (2013.01); *C11D 3/38618* (2013.01); *C11D 3/38681* (2013.01); *C11D 11/0023* (2013.01); *C12N 9/2414* (2013.01); *C12N 9/2417* (2013.01); *C12Y 302/01001* (2013.01)

(58) Field of Classification Search
None
See application file for complete search history.

(56) References Cited

U.S. PATENT DOCUMENTS 6,143,708 A * 11/2000 Svendsen ............... C11D 3/386
435/202
2011/0195481 A1 8/2011 Svendsen

FOREIGN PATENT DOCUMENTS

| EP | 2 465 930 A2 | 6/2012 |
|---|---|---|
| WO | 2007/079938 A2 | 7/2007 |
| WO | 2009/061380 A2 | 5/2009 |
| WO | 2010/115021 A2 | 10/2010 |
| WO | 2013/057141 A2 | 4/2013 |
| WO | 2014/164777 A1 | 10/2014 |
| WO | 2014/195356 A2 | 12/2014 |

OTHER PUBLICATIONS

Igarashi et al, 1998, Biochem Biophys Res Com 248, 372-377.
Shiau et al, 2003, Appl Environ Microbiol 69(4), 2383-2385.
Suzuki et al, 1989, The J of Biological Chem 264(32), 18933-18938.

* cited by examiner

*Primary Examiner* — David Steadman
(74) *Attorney, Agent, or Firm* — David Fazzolare

(57) ABSTRACT

The present invention relates to alpha-amylase variants having an improved stability as compared to the parent alpha-amylase. The invention further relates to use of the variants, compositions comprising the variants, and methods of producing the variants.

21 Claims, No Drawings
Specification includes a Sequence Listing.

STABILIZED ALPHA-AMYLASE VARIANTS AND USE OF THE SAME

CROSS-REFERENCE TO RELATED APPLICATIONS

This application claims priority or the benefit under 35 U.S.C. 119 of Danish application no. PA 2016 00210 filed Apr. 8, 2016, the contents of which are fully incorporated herein by reference.

REFERENCE TO A SEQUENCE LISTING

This application contains a Sequence Listing in computer readable form, which is incorporated herein by reference.

BACKGROUND OF THE INVENTION

Field of the Invention

The present invention relates to stabilized alpha-amylase variants, polynucleotides encoding the variants, methods of producing the variants, and methods of using the variants.

Description of the Related Art

Alpha-amylases (alpha-1,4-glucan-4-glucanohydrolases, E.C. 3.2.1.1) constitute a group of enzymes, which catalyzes hydrolysis of starch and other linear and branched 1,4-gluosidic oligo- and polysaccharides.

There is a long history of industrial use of alpha-amylases in several known applications such as detergent, baking, brewing, starch liquefaction and saccharification e.g. in preparation of high fructose syrups or as part of ethanol production from starch. These and other applications of alpha-amylases are known and utilize alpha-amylases derived from microorganisms, in particular bacterial alpha-amylases.

Among the first bacterial alpha-amylases to be used were an alpha-amylase from *B. licheniformis*, also known as Termamyl which have been extensively characterized and the crystal structure has been determined for this enzyme. *Bacillus* amylases, such as Termamyl and SP707, form a particular group of alpha-amylases that have found use in detergents. Many of these known bacterial amylases have been modified in order to improve their functionality in a particular application.

Methods of increasing the thermostability of alpha-amylases have been well studied. Suzuki et al. (1989) disclose chimeric alpha-amylases, in which specified regions of a *B. amyloliquefaciens* alpha-amylase have been substituted for the corresponding regions of a *B. licheniformis* alpha-amylase. The chimeric alpha-amylases were constructed with the purpose of identifying regions responsible for thermostability. Such regions were found to include amino acid residues 177-186 and amino acid residues 255-270 of the *B. amyloliquefaciens* alpha-amylase. Igarashi et al. 1998 show that the thermostability of AmyS-type amylases can be increased by the deletion of two amino acid residues, R179-G180, (AmyS numbering) from a loop (F178 to A184). However, Shiau et al. (2003) showed that an AmyS enzyme with deletion in the same loop has a lower specific activity for corn starch hydrolysis at high-temperature than the parent enzyme, negating one of the principal advantages of AmyS amylases.

In WO 2014/195356 alpha-amylase variants such as the *Bacillus* TS-23 alpha-amylase are described to have improved stability. The variants may have i) a deletion at two or more positions and ii) an alteration at one or more positions selected from a list.

For environmental reasons it has been increasingly important to lower the temperature in washing, dishwashing and/or cleaning processes. However, most enzymes including amylases have a temperature optimum which is above the temperature usually used in low temperature washing. Alpha-amylase is a key enzyme for use in detergent compositions and its use has become increasingly important for removal of starchy stains during laundry washing or dishwashing. Therefore, it is important to find alpha-amylase variants, which retain their wash performance, stain removal effect and/or activity when the temperature is lowered. However, despite the efficiency of current detergents enzyme compositions, there are many stains that are difficult to completely remove. These problems are compounded by the increased use of low (e.g., cold water) wash temperatures and shorter washing cycles. Thus, it is desirable to have amylolytic enzymes that can function under low temperature and at the same time preserve or increase other desirable properties such as specific activity (amylolytic activity), stability and/or wash performance.

Thus, it is an object of the present invention to provide alpha-amylase variants that exhibit a high level of stability when incorporated into detergent compositions such as liquid detergents, in particular in the presence of chelating agents, surfactants, proteases and/or alkaline conditions.

The present invention provides alpha-amylase variants with improved stability compared to its parent and to known alpha-amylase variants.

SUMMARY OF THE INVENTION

In one aspect, the present invention relates to a variant of a parent alpha-amylase, the variant has alpha-amylase activity and has at least 89% sequence identity to SEQ ID NO: 1, wherein the variant comprises an amino acid motif of FX1X2K at positions corresponding to amino acid 180 to 183 of SEQ ID NO: 2; wherein X1 is R or S, and X2 may be selected from A, R, N, D, C, E, Q, G, H, I, L, K, M, F, P, S, T, W, Y, and V with the proviso that when X1 is R, then X2 is not S and wherein said variant has an improved Residual Activity (RA) compared to an amylase comprising the motif FRSK (SEQ ID NO: 7).

In a further aspect, the present invention relates to a composition comprising a variant of the invention.

In a further aspect, the present invention relates to a detergent additive comprising a variant of the invention, optionally in the form of a non-dusting granulate, stabilized liquid, or protected enzyme.

In a further aspect, the present invention to a manual or automatic dishwashing detergent composition comprising a variant of the invention, and optionally a surfactant.

In a further aspect, the present invention relates to a manual or automatic laundry detergent composition comprising a variant of the invention.

In a further aspect, the present invention relates to the use of the variant of the invention.

In one aspect, the present invention relates to the use of the variant of the invention in laundry, dishwash; such as automatic or manual dish wash, hard surface cleaning, industrial and institutional cleaning, textile desizing, starch modification, starch liquefaction, saccharification, feed, baking or brewing.

In a further aspect, the present invention relates to a polynucleotide encoding the variant of the invention.

In one aspect, the present invention relates to a nucleic acid construct comprising the polypeptide of the invention.

In one aspect, the present invention relates to an expression vector comprising the polypeptide of the invention.

In one aspect, the present invention relates to a host cell comprising the polypeptide of the invention.

In a further aspect, the present invention relates to a method of producing an alpha-amylase variant of the invention, comprising (a) cultivating the host cell of the invention under conditions suitable for expression of said variant; and (b) recovering the variant.

In a further aspect, the present invention relates to a method for obtaining an alpha-amylase variant, comprising introducing into a parent alpha-amylase a deletion of two amino acids selected from the position corresponding to R180, S181, T182, and G183 of the amino acid sequence of SEQ ID NO: 1 providing an amino acid motif of FX1X2K (SEQ ID NO: 4), wherein X1 is R or S; and X2 may be selected from A, R, N, D, C, E, Q, G, H, I, L, K, M, F, P, S, T, W, Y, and V with the proviso that when X1 is R, then X2 is not S, said variant has an improved Residual Activity (RA) compared to an amylase comprising the motif FRSK (SEQ ID NO: 7), and wherein said variant has alpha-amylase activity; and recovering the variant.

Definitions

Alpha-amylase: The term "alpha-amylase activity" as used herein, refers to the activity of alpha-1,4-glucan-4-glucanohydrolases, E.C. 3.2.1.1, which constitute a group of enzymes, which catalyze hydrolysis of starch and other linear and branched 1,4-glucosidic oligo- and polysaccharides. For purposes of the present invention, alpha-amylase activity is determined according to the procedure described in the Methods. In one aspect, the variants of the present invention have at least 20%, e.g., at least 40%, at least 50%, at least 60%, at least 70%, at least 80%, at least 90%, at least 95%, or at least 100% of the alpha-amylase activity of the mature polypeptide of SEQ ID NO: 1, 2, or 3 as set out below:

SEQ ID NO: 1

(SEQ ID NO: 1)
NTAPINETMMQYFEWDLPNDGTLWTKVKNEAANLSSLGITALWLPPAYKG

TSQSDVGYGVYDLYDLGEFNQKGTIRTKYGTKTQYIQAIQAAKAAGMQVY

ADVVFNHKAGADGTEFVDAVEVDPSNRNQETSGTYQIQAWTKFDFPGRGN

TYSSFKWRWYHFDGTDWDESRKLNRIYKFRSTGKAWDWEVDTENGNYDYL

MFADLDMDHPEVVTELKNWGTWYVNTTNIDGFRLDAVKHIKYTFFPDWLT

YVRNQTGKNLFAVGEFWSYDVNKLHNYITKTNGSMSLFDAPLHNNFYTAS

KSSGYFDMRYLLNNTLMKDQPSLAVTLVDNHDTQPGQSLQSWVEPWFKPL

AYAFILTRQEGYPCVFYGDYYGIPKYNIPGLKSKIDPLLIARRDYAYGTQ

RDYIDHQDIIGWTREGIDTKPNSGLAALITDGPGGSKWMYVGKKHAGKVF

YDLTGNRSDTVTINADGWGEFKVNGGSVSIWVAK

SEQ ID NO: 2

(SEQ ID NO: 2)
NTAPINETMMQYFEWDLPNDGTLWTKVKNEAANLSSLGITALWLPPAYKG

TSQSDVGYGVYDLYDLGEFNQKGTIRTKYGTKTQYIQAIQAAKAAGMQVY

ADVVFNHKAGADGTEFVDAVEVDPSNRNQETSGTYQIQAWTKFDFPGRGN

TYSSFKWRWYHFDGTDWDESRKLNRIYKFX1X2KAWDWEVDTENGNYDYL

MFADLDMDHPEVVTELKNWGTWYVNTTNIDGFRLDAVKHIKYTFFPDWLT

YVRNQTGKNLFAVGEFWSYDVNKLHNYITKTNGSMSLFDAPLHNNFYTAS

KSSGYFDMRYLLNNTLMKDQPSLAVTLVDNHDTQPGQSLQSWVEPWFKPL

AYAFILTRQEGYPCVFYGDYYGIPKYNIPGLKSKIDPLLIARRDYAYGTQ

RDYIDHQDIIGWTREGIDTKPNSGLAALITDGPGGSKWMYVGKKHAGKVF

YDLTGNRSDTVTINADGWGEFKVNGGSVSIWVAK

SEQ ID NO: 3

(SEQ ID NO: 3)
NTAPINETMMQYFEWDLPNDGTLWTKVKNEAANLSSLGITALWLPPAYKG

TSQSDVGYGVYDLYDLGEFNQKGTIRTKYGTKTQYIQAIQAAKAAGMQVY

ADVVFNHKAGADGTEFVDAVEVDPSNRNQETSGTYQIQAWTKFDFPGRGN

TYSSFKWRWYHFDGTDWDESRKLNRIYKFRSTGKAWDWEVDTENGNYDYL

MFADLDMDHPEVVTELKNWGTWYVNTTNIDGFRLDAVKHIKYSFFPDWLT

YVRNQTGKNLFAVGEFWSYDVNKLHNYITKTNGSMSLFDAPLHNNFYTAS

KSSGYFDMRYLLNNTLMKDQPSLAVTLVDNHDTQPGQSLQSWVEPWFKPL

AYAFILTRQEGYPCVFYGDYYGIPKYNIPGLKSKIDPLLIARRDYAYGTQ

RDYIDHQDIIGWTREGIDTKPNSGLAALITDGPGGSKWMYVGKKHAGKVF

YDLTGNRSDTVTINADGWGEFKVNGGSVSIWVAKTSNVTFTVNNATTTSG

QNVYVVANIPELGNWNTANAIKMNPSSYPTWKATIALPQGKAIEFKFIKK

DQAGNVIWESTSNRTYTVPFSSTGSYTASWNVP

SEQ ID NO: 4

(SEQ ID NO: 4)
FX1X2K

Alpha-amylase activity: The term 'alpha-amylase activity' as used herein, refers to the activity of an alpha-amylase wherein the activity is determined according to the procedure described in the Methods. The alpha-amylase activity may be determined according to a method using the Phadebas assay which is described in the Example 1. Other alpha-amylase activity assays, such as EnzCheck or Amylazyme, may be used.

Amino acid: The term 'amino acid' as used herein, refers to the standard twenty genetically-encoded amino acids and their corresponding stereoisomers in the 'd' form (as compared to the natural 'l' form), omega-amino acids other naturally-occurring amino acids, unconventional amino acids (e.g. α, α-disubstituted amino acids, N-alkyl amino acids, etc.) and chemically derivatised amino acids. Chemical derivatives of one or more amino acids may be achieved by reaction with a functional side group. Such derivatised molecules include, for example, those molecules in which free amino groups have been derivatised to form amine hydrochlorides, p-toluene sulphonyl groups, carboxybenzoxy groups, t-butyloxycarbonyl groups, chloroacetyl groups or formyl groups. Free carboxyl groups may be derivatised to form salts, methyl and ethyl esters or other types of esters and hydrazides. Free hydroxyl groups may be derivatised to form O-acyl or O-alkyl derivatives. Also included as chemical derivatives are those peptides which contain naturally occurring amino acid derivatives of the twenty standard amino acids. For example: 4-hydroxyproline may be substituted for proline; 5-hydroxylysine may be substituted for lysine; 3-methylhistidine may be substituted for histidine; homoserine may be substituted for serine and ornithine for lysine. Derivatives also include peptides containing one or more additions or deletions as long as the requisite activity is maintained. Other included modifications are amidation, amino terminal acylation (e.g. acetylation or thioglycolic acid amidation), terminal carboxylamidation (e.g. with ammonia or methylamine), and the like terminal modifications.

When an amino acid is being specifically enumerated, such as 'alanine' or 'Ala' or 'A', the term refers to both l-alanine and d-alanine unless explicitly stated otherwise. Other unconventional amino acids may also be suitable components for polypeptides of the present invention, as long as the desired functional property is retained by the polypeptide. For the peptides shown, each encoded amino acid residue, where appropriate, is represented by a single letter designation, corresponding to the trivial name of the conventional amino acid. In one embodiment, the polypeptides of the invention comprise or consist of I-amino acids.

Amino acid motif: The term "amino acid motif" or "the motif" as used herein, refers to a specifically defined amino acid stretch of a polypeptide. Thus, an amino acid motif relates to a short sequence of amino acids in a parent polypeptide. According to the present invention, the amino acid motif corresponds to SEQ ID NO: 4 corresponding to amino acid positions 180 to 183 of SEQ ID NO: 2.

cDNA: The term "cDNA" as used herein, refers to a DNA molecule that can be prepared by reverse transcription from a mature, spliced, mRNA molecule obtained from a eukaryotic or prokaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

Coding sequence: The term "coding sequence" as used herein, refers to a polynucleotide, which directly specifies the amino acid sequence of a variant. The boundaries of the coding sequence are generally determined by an open reading frame, which begins with a start codon such as ATG, GTG or TTG and ends with a stop codon such as TAA, TAG, or TGA. The coding sequence may be a genomic DNA, cDNA, synthetic DNA, or a combination thereof.

Control sequences: The term "control sequences" as used herein, refers to nucleic acid sequences necessary for expression of a polynucleotide encoding a variant of the present invention. Each control sequence may be native (i.e., from the same gene) or foreign (i.e., from a different gene) to the polynucleotide encoding the variant or native or foreign to each other. Such control sequences include, but are not limited to, a leader, polyadenylation sequence, pro-peptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a variant.

Corresponding to: The term "corresponding to" as used herein, refers to a way of determining the specific amino acid of a sequence wherein reference is made to a specific amino acid sequence. E.g. for the purposes of the present invention, when references are made to specific amino acid positions, the skilled person would be able to align another amino acid sequence to said amino acid sequence that reference has been made to, in order to determine which specific amino acid may be of interest in said another amino acid sequence. Alignment of another amino acid sequence with e.g. the sequence as set forth in SEQ ID NO: 1, 2, or 3, or any other sequence listed herein, has been described elsewhere herein. Alternative alignment methods may be used, and are well-known for the skilled person.

Dish washing composition: The term "dish washing composition" as used herein, refers to all forms of compositions for cleaning hard surfaces. The present invention is not restricted to any particular type of dish wash composition or any particular detergent. Thus, in one embodiment, the dish washing composition is a liquid dish washing composition, a powder dish washing composition, wherein the composition may optionally be in the form of a unit dose.

Enzyme Detergency benefit: The term "enzyme detergency benefit" used herein, refers to the advantageous effect an enzyme may add to a detergent compared to the same detergent without the enzyme. Important detergency benefits which can be provided by enzymes are stain removal with no or very little visible soils after washing and/or cleaning, prevention or reduction of re-deposition of soils released in the washing process (an effect that also is termed antiredeposition), restoring fully or partly the whiteness of textiles which originally were white but after repeated use and wash have obtained a greyish or yellowish appearance (an effect that also is termed whitening). Textile care benefits, which are not directly related to catalytic stain removal or prevention of re-deposition of soils, are also important for enzyme detergency benefits. Examples of such textile care benefits are prevention or reduction of dye transfer from one fabric to another fabric or another part of the same fabric (an effect that is also termed dye transfer inhibition or anti-backstaining), removal of protruding or broken fibers from a fabric surface to decrease pilling tendencies or remove already existing pills or fuzz (an effect that also is termed anti-pilling), improvement of the fabric-softness, colour clarification of the fabric and removal of particulate soils which are trapped in the fibers of the fabric or garment. Enzymatic bleaching is a further enzyme detergency benefit where the catalytic activity generally is used to catalyze the formation of bleaching component such as hydrogen peroxide or other peroxides.

Expression: The term "expression" as used herein, refers to any step involved in the production of a variant including, but not limited to, transcription, post-transcriptional modification, translation, post-translational modification, and secretion.

Expression vector: The term "expression vector" as used herein, refers to a linear or circular DNA molecule that comprises a polynucleotide encoding a variant and is operably linked to control sequences that provide for its expression.

Fragment: The term "fragment" as used herein, refers to a polypeptide having one or more (e.g., several) amino acids absent from the amino and/or carboxyl terminus of the mature polypeptide of SEQ ID NO:1; wherein the fragment has alpha-amylase activity. In one aspect, a fragment contains at least 200 contiguous amino acid residues of SEQ ID NO: 1, for example at least 300 contiguous amino acid residues, or at least 350 contiguous amino acid residues, or at least 400 contiguous amino acid residues, or at least 450 contiguous amino acid residues of SEQ ID NO: 1.

Hard surface cleaning: The term "hard surface cleaning" as used herein, refers to cleaning of hard surfaces wherein hard surfaces may include floors, tables, walls, roofs etc. as well as surfaces of hard objects such as cars (car wash) and dishes (dish wash). Dish washing includes but are not limited to cleaning of plates, cups, glasses, bowls, cutlery such as spoons, knives, forks, serving utensils, ceramics, plastics, metals, china, glass and acrylics Host cell: The term "host cell" as used herein, refers to any cell type that is susceptible to transformation, transfection, transduction, or the like with a nucleic acid construct or expression vector comprising a polynucleotide of the present invention. The term "host cell" encompasses any progeny of a parent cell that is not identical to the parent cell due to mutations that occur during replication.

Intensity value: The wash performance is measured as the brightness expressed as the intensity of the light reflected from the sample when illuminated with white light. When the sample is stained the intensity of the reflected light is lower, than that of a clean sample. Therefore, the intensity of the reflected light can be used to measure wash performance, where a higher intensity value correlates with higher wash performance. Color measurements are made with a professional flatbed scanner (Kodak iQsmart, Kodak) used to capture an image of the washed textile. To extract a value for the light intensity from the scanned images, 24-bit pixel values from the image are converted into values for red, green and blue (RGB). The intensity value (Int) is calculated by adding the RGB values together as vectors and then taking the length of the resulting vector:

$$Int = \sqrt{r^2 + g^2 + b^2}$$

Improved property: The term "improved property" as used herein, refers to a characteristic associated with a variant that is improved compared to the parent. Such improved properties include, but are not limited to, wash performance and stability under storage conditions. The improved property may be any of those herein defined and described, such as stability.

Isolated: The term "isolated" as used herein, refers to a substance in a form or environment which does not occur in nature. Non-limiting examples of isolated substances include (1) any non-naturally occurring substance, (2) any substance including, but not limited to, any enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., multiple copies of a gene encoding the substance; use of a stronger promoter than the promoter naturally associated with the gene encoding the substance). An isolated substance may be present in a fermentation broth sample.

Mature polypeptide: The term "mature polypeptide" as used herein, refers to means a polypeptide in its final form following translation and any post-translational modifications, such as N-terminal processing, C-terminal truncation, glycosylation, phosphorylation, etc. It is known in the art that a host cell may produce a mixture of two of more different mature polypeptides (i.e., with a different C-terminal and/or N-terminal amino acid) expressed by the same polynucleotide.

Mature polypeptide coding sequence: The term "mature polypeptide coding sequence" as used herein, refers to a polynucleotide that encodes a mature polypeptide having alpha-amylase activity.

Modification: The term "modification", in the context of the polypeptides of the invention, means that one or more amino acids within the reference amino acid sequence (i.e. SEQ ID NO:1, 2, or 3) are altered by substitution with a different amino acid, by insertion of an amino acid or by deletion. Additionally, the mutation may correspond to an insertion of one or more extra amino acid(s) within the reference amino acid sequence. The terms "modification", "alteration", and "mutation" may be used interchangeably and constitute the same meaning and purpose.

Nucleic acid construct: The term "nucleic acid construct" as used herein, refers to a nucleic acid molecule, either single- or double-stranded, which is isolated from a naturally occurring gene or is modified to contain segments of nucleic acids in a manner that would not otherwise exist in nature or which is synthetic, which comprises one or more control sequences.

Operably linked: The term "operably linked" as used herein, refers to a configuration in which a control sequence is placed at an appropriate position relative to the coding sequence of a polynucleotide such that the control sequence directs expression of the coding sequence.

Parent or parent alpha-amylase: The term "parent" or "parent alpha-amylase" as used herein, refers to the alpha-amylase of SEQ ID NO:1, 2, or 3, or any alpha-amylase having at least 89% sequence identity to any of the polypeptides of SEQ ID NO: 1, 2, or 3. The parent amylase may also be a polypeptide comprising a fragment of SEQ ID NO: 1, 2, or 3, i.e. the parent alpha-amylase may be a fusion polypeptide having alpha-amylase activity as defined elsewhere herein.

Residual Activity (RA): The term "Residual Activity (RA)" as used herein refers to the activity that remains of a variant according to the invention and/or an enzyme after incubation at a certain temperature for a certain time period. The RA may be determined as described in Example 1 by use of e.g. Phadebas assay.

Starch modification: The term "starch modification" as used herein refers to a process where starch is degraded upon production of paper pulp in the paper industry. Paper desizing may be used in the paper industry processes in order to obtain an optimal viscosity of the paper pulp.

Sequence identity: The relatedness between two amino acid sequences or between two nucleotide sequences is described by the parameter "sequence identity".

For purposes of the present invention, the sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used may be gap open penalty of 10, gap extension penalty of 0.5, and the EBLOSUM62 (EMBOSS version of BLOSUM62) substitution matrix. The output of Needle labeled "longest identity" (obtained using the no-brief option) is used as the percent identity and is calculated as follows:

(Identical Residues×100)/(Length of Alignment—Total Number of Gaps in Alignment)

Alternatively, the parameters used may be gap open penalty of 10, gap extension penalty of 0.5, and the EDNAFULL (EMBOSS version of NCBI NUC4.4) substitution matrix. The output of Needle labeled "longest identity" (obtained using the no-brief option) is used as the percent identity and is calculated as follows:

(Identical Deoxyribonucleotides×100)/(Length of Alignment—Total Number of Gaps in Alignment)

Subsequence: The term "subsequence" as used herein, refers to a polynucleotide having one or more (e.g., several)

nucleotides absent from the 5' and/or 3' end of a mature polypeptide coding sequence; wherein the subsequence encodes a fragment having alpha-amylase activity.

Textile: Textile sample CS-28 (rice starch on cotton) is obtained from Center For Testmaterials BV, P.O. Box 120, 3133 KT Vlaardingen, the Netherlands.

Textile care benefit: The term "textile care benefits", as used herein, is defined as not being directly related to catalytic stain removal or prevention of re-deposition of soils, are also important for enzyme detergency benefits. Examples of such textile care benefits are prevention or reduction of dye transfer from one textile to another textile or another part of the same textile (an effect that is also termed dye transfer inhibition or anti-backstaining), removal of protruding or broken fibers from a textile surface to decrease pilling tendencies or remove already existing pills or fuzz (an effect that also is termed anti-pilling), improvement of the textile-softness, colour clarification of the textile and removal of particulate soils which are trapped in the fibers of the textile. Enzymatic bleaching is a further enzyme detergency benefit where the catalytic activity generally is used to catalyze the formation of bleaching component such as hydrogen peroxide or other peroxides or other bleaching species."

Variant: The term "variant" as used herein, refers to a polypeptide having alpha-amylase activity comprising a mutation, i.e., a substitution, insertion, and/or deletion, at one or more (e.g., several) positions relative to the 'parent' alpha-amylase of SEQ ID NO:1. A substitution means replacement of the amino acid occupying a position with a different amino acid; a deletion means removal of the amino acid occupying a position; and an insertion means adding an amino acid adjacent to and immediately following the amino acid occupying a position. The variants of the present invention have at least 20%, e.g., at least 40%, at least 50%, at least 60%, at least 70%, at least 80%, at least 90%, at least 95%, or at least 100% of the alpha-amylase activity of the mature polypeptide of SEQ ID NO: 1, 2, or 3.

Wild-type alpha-amylase: The term "wild-type alpha-amylase" as used herein refers to an alpha-amylase expressed by a naturally occurring microorganism, such as a bacterium, yeast, or filamentous fungus found in nature.

Conventions for Designation of Variants

The polypeptides of the invention having the invention having alpha-amylase activity correspond to variants of an alpha-amylase derived from Bacillus, as shown in SEQ ID NO: 1, 2, or 3.

SEQ ID NO: 1
(SEQ ID NO: 1)
NTAPINETMMQYFEWDLPNDGTLWTKVKNEAANLSSLGITALWLPPAYKG

TSQSDVGYGVYDLYDLGEFNQKGTIRTKYGTKTQYIQAIQAAKAAGMQVY

ADVVFNHKAGADGTEFVDAVEVDPSNRNQETSGTYQIQAWTKFDFPGRGN

TYSSFKWRWYHFDGTDWDESRKLNRIYKFRSTGKAWDWEVDTENGNYDYL

MFADLDMDHPEVVTELKNWGTWYVNTTNIDGFRLDAVKHIKYTFFPDWLT

YVRNQTGKNLFAVGEFWSYDVNKLHNYITKTNGSMSLFDAPLHNNFYTAS

KSSGYFDMRYLLNNTLMKDQPSLAVTLVDNHDTQPGQSLQSWVEPWFKPL

AYAFILTRQEGYPCVFYGDYYGIPKYNIPGLKSKIDPLLIARRDYAYGTQ

RDYIDHQDIIGWTREGIDTKPNSGLAALITDGPGGSKWMYVGKKHAGKVF

YDLTGNRSDTVTINADGWGEFKVNGGSVSIWVAK

The variant, i.e. mutated, amino acids in the polypeptides of the invention are defined by reference to the amino acid numbering of SEQ ID NO: 1 (which corresponds to the mature protein TS23 of Bacillus sp. TS-23). The amino acid sequence differences relative to SEQ ID NO: 1 are shown below in bold, underlined. The amino acid sequences of SEQ ID NO: 1 and 2 are identical with except of the highlighted positions X1 and X2 of SEQ ID NO: 2.

SEQ ID NO: 2
(SEQ ID NO: 2)
NTAPINETMMQYFEWDLPNDGTLWTKVKNEAANLSSLGITALWLPPAYKG

TSQSDVGYGVYDLYDLGEFNQKGTIRTKYGTKTQYIQAIQAAKAAGMQVY

ADVVFNHKAGADGTEFVDAVEVDPSNRNQETSGTYQIQAWTKFDFPGRGN

TYSSFKWRWYHFDGTDWDESRKLNRIYKFX1X2KAWDWEVDTENGNYDYL

MFADLDMDHPEVVTELKNWGTWYVNTTNIDGFRLDAVKHIKYTFFPDWLT

YVRNQTGKNLFAVGEFWSYDVNKLHNYITKTNGSMSLFDAPLHNNFYTAS

KSSGYFDMRYLLNNTLMKDQPSLAVTLVDNHDTQPGQSLQSWVEPWFKPL

AYAFILTRQEGYPCVFYGDYYGIPKYNIPGLKSKIDPLLIARRDYAYGTQ

RDYIDHQDIIGWTREGIDTKPNSGLAALITDGPGGSKWMYVGKKHAGKVF

YDLTGNRSDTVTINADGWGEFKVNGGSVSIWVAK

For the purposes of the present invention, the mature polypeptide disclosed in SEQ ID NO: 1 is used to determine the corresponding amino acid residue in another alpha-amylase polypeptide. However, the skilled person would recognize that the sequence of SEQ ID NO: 2 may also be used to determine the corresponding amino acid residue in another alpha-amylase polypeptide. The amino acid sequence of another alpha-amylase is aligned with the mature polypeptide disclosed in SEQ ID NO: 1, and based on the alignment, the amino acid position number corresponding the any amino acid residue in the mature polypeptide disclosed in SEQ ID NO: 1 is determined using the Needleman-Wunsch algorithm (Needleman and Wunsch, 1970, J. Mol. Biol. 48: 443-453) as implemented in the Needle program of the EMBOSS package (EMBOSS: The European Molecular Biology Open Software Suite, Rice et al., 2000, Trends Genet. 16: 276-277), preferably version 5.0.0 or later. The parameters used are gap open penalty of 10, gap extension penalty of 0.5, and the EBLOSUM62 (EMBOSS version of BLOSUM62) substitution matrix.

Identification of the corresponding amino acid residue in another alpha-amylase can be determined by an alignment of multiple polypeptide sequences using several computer programs including, but not limited to, MUSCLE (multiple sequence comparison by log-expectation; version 3.5 or later; Edgar, 2004, Nucleic Acids Research 32: 1792-1797), MAFFT (version 6.857 or later; Katoh and Kuma, 2002, Nucleic Acids Research 30: 3059-3066; Katoh et al., 2005, Nucleic Acids Research 33: 511-518; Katoh and Toh, 2007, Bioinformatics 23: 372-374; Katoh et al., 2009, Methods in Molecular Biology 537: 39-64; Katoh and Toh, 2010, Bioinformatics 26: 1899-1900), and EMBOSS EMMA employing ClustalW (1.83 or later; Thompson et al., 1994, Nucleic Acids Research 22: 4673-4680), using their respective default parameters.

When the other alpha-amylase has diverged from the mature polypeptide of SEQ ID NO: 1 such that traditional sequence-based comparison fails to detect their relationship (Lindahl and Elofsson, 2000, J. Mol. Biol. 295: 613-615), other pairwise sequence comparison algorithms can be used. Greater sensitivity in sequence-based searching can be attained using search programs that utilize probabilistic representations of polypeptide families (profiles) to search databases. For example, the PSI-BLAST program generates profiles through an iterative database search process and is capable of detecting remote homologs (Atschul et al., 1997, *Nucleic Acids Res.* 25: 3389-3402). Even greater sensitivity can be achieved if the family or superfamily for the polypeptide has one or more representatives in the protein structure databases. Programs such as GenTHREADER (Jones, 1999, *J. Mol. Biol.* 287: 797-815; McGuffin and Jones, 2003, *Bioinformatics* 19: 874-881) utilize information from a variety of sources (PSI-BLAST, secondary structure prediction, structural alignment profiles, and solvation potentials) as input to a neural network that predicts the structural fold for a query sequence. Similarly, the method of Gough et al., 2000, *J. Mol. Biol.* 313: 903-919, can be used to align a sequence of unknown structure with the superfamily models present in the SCOP database. These alignments can in turn be used to generate homology models for the polypeptide, and such models can be assessed for accuracy using a variety of tools developed for that purpose.

For proteins of known structure, several tools and resources are available for retrieving and generating structural alignments. For example the SCOP superfamilies of proteins have been structurally aligned, and those alignments are accessible and downloadable. Two or more protein structures can be aligned using a variety of algorithms such as the distance alignment matrix (Holm and Sander, 1998, *Proteins* 33: 88-96) or combinatorial extension (Shindyalov and Bourne, 1998, *Protein Engineering* 11: 739-747), and implementation of these algorithms can additionally be utilized to query structure databases with a structure of interest in order to discover possible structural homologs (e.g., Holm and Park, 2000, *Bioinformatics* 16: 566-567).

In describing the alpha-amylase variants of the present invention, the nomenclature described below is adapted for ease of reference. The accepted IUPAC single letter or three letter amino acid abbreviation is employed.

Substitutions.

For an amino acid substitution, the following nomenclature is used: Original amino acid, position, substituted amino acid. Accordingly, the substitution of e.g. threonine at position 226 with alanine is designated as "Thr226Ala" or "T226A". Multiple mutations are separated by addition marks ("+"), e.g., "Gly205Arg+Ser411Phe" or "G205R+S411F", representing substitutions at positions 205 and 411 of glycine (G) with arginine (R) and serine (S) with phenylalanine (F), respectively.

Deletions.

For an amino acid deletion, the following nomenclature is used: Original amino acid, position, *. Accordingly, the deletion of glycine at position 181 is designated as "Ser181*" or "S181*". Multiple deletions are separated by addition marks ("+"), e.g., "Ser181*+Thr182*" or "S181*+T182*".

Insertions.

For an amino acid insertion, the following nomenclature is used: Original amino acid, position, original amino acid, inserted amino acid. Accordingly the insertion of lysine after e.g. glycine at position 195 is designated "Gly195GlyLys" or "G195GK". An insertion of multiple amino acids is designated [Original amino acid, position, original amino acid, inserted amino acid #1, inserted amino acid #2; etc.].

For example, the insertion of lysine and alanine after glycine at position 195 is indicated as "Gly195GlyLysAla" or "G195GKA".

In such cases the inserted amino acid residue(s) are numbered by the addition of lower case letters to the position number of the amino acid residue preceding the inserted amino acid residue(s). In the above example, the sequence would thus be:

| Parent: | Variant: |
|---------|----------|
| 195     | 195 195a 195b |
| G       | G-K-A    |

Multiple Alterations.

Variants comprising multiple alterations are separated by addition marks ("+"), e.g., "Arg170Tyr+Gly195Glu" or "R170Y+G195E" representing a substitution of arginine and glycine at positions 170 and 195 with tyrosine and glutamic acid, respectively.

Different Alterations.

Where different alterations can be introduced at a position, the different alterations are separated by a comma, e.g., "Arg170Tyr,Glu" represents a substitution of arginine at position 170 with tyrosine or glutamic acid. Thus, "Tyr167Gly,Ala+Arg170Gly,Ala" designates the following variants:

"Tyr167Gly+Arg170Gly", "Tyr167Gly+Arg170Ala", "Tyr167Ala+Arg170Gly", and "Tyr167Ala+Arg170Ala".

DETAILED DESCRIPTION OF THE INVENTION

The present invention relates to a variant of a parent alpha-amylase, said variant has alpha-amylase activity and has at least 89% sequence identity to SEQ ID NO: 1, wherein said variant comprises an amino acid motif of FX1X2K (SEQ ID NO: 4) at positions corresponding to amino acids 180 to 183 of SEQ ID NO: 2; wherein X1 is R or S; and X2 may be selected from A, R, N, D, C, E, Q, G, H, I, L, K, M, F, P, S, T, W, Y, and V with the proviso that when X1 is R, then X2 is not S and wherein said variant has an improved Residual Activity (RA) compared to an amylase comprising the motif FRSK (SEQ ID NO: 7).

The present invention provides a variant of a parent alpha-amylase which has shown to have a significantly improved stability as compared to known homologous alpha-amylase variants, i.e. variants of backbones having less than 89% sequence identity to SEQ ID NO: 1, and wherein the variants have similar motif as the present invention. In particular, as can be seen from Example 2, comparative data with similar variants in a distant alpha-amylase (SP722), the variants of the present invention have significant improved stability. Thus, without being bound by theory, it is believed that deletion variants as those of the present invention cannot be expected to show the same stability pattern as known deletion variants of e.g. SP722.

In one embodiment, the variant has at least 89%, such as 90%, such as 91%, such as 92%, such as 93%, such as 94%, such as 95%, such as 96%, such as 97%, such as 98%, such as 99%, but less than 100% sequence identity to SEQ ID NO: 1.

In one embodiment, X2 of SEQ ID NO: 2 is an S, G, or T. Thus, in one embodiment, X2 is S, G, or T.

In another embodiment, X1 of SEQ ID NO: 2 is an R, then X2 of SEQ ID NO: 2 is G, or T. Thus, in one embodiment, when X1 is R, X2 is G, or T.

In another embodiment, X1 of SEQ ID NO: 2 is S, then X2 of SEQ ID NO: 2 is S, G, or T. Thus, in one embodiment, when X1 is S, X2 is S, G, or T.

In another particular embodiment, X1 of SEQ ID NO: 2 is R, and X2 of SEQ ID NO: 2 is G. Thus, in one particular embodiment, X1 is R, and X2 is G.

In another particular embodiment, X1 of SEQ ID NO: 2 is R, and X2 of SEQ ID NO: 2 is T. Thus, in one particular embodiment, X1 is R and X2 is T.

In another particular embodiment, X1 of SEQ ID NO: 2 is S, and X2 of SEQ ID NO: 2 is T. Thus, in one particular embodiment, X1 is S, and X2 is T.

In another particular embodiment, X1 of SEQ ID NO: 2 is S, and X2 of SEQ ID NO: 2 is G. Thus, in one particular embodiment, X1 is S, and X2 is G.

The variants of the present invention may further comprise one or more additional modifications at one or more (e.g., several) other positions.

The amino acid changes may be of a minor nature, that is conservative amino acid substitutions or insertions that do not significantly affect the folding and/or activity of the protein; small deletions, typically of 1 to 30 amino acids; small amino- or carboxyl-terminal extensions, such as an amino-terminal methionine residue; a small linker peptide of up to 20 to 25 residues; or a small extension that facilitates purification by changing net charge or another function, such as a poly-histidine tract, an antigenic epitope or a binding domain.

Examples of conservative substitutions are within the groups of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, In, *The Proteins*, Academic Press, New York. Common substitutions are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

Alternatively, the amino acid changes are of such a nature that the physico-chemical properties of the polypeptides are altered. For example, amino acid changes may improve the thermal stability of the polypeptide, alter the substrate specificity, change the pH optimum, and the like.

Essential amino acids in a polypeptide can be identified according to procedures known in the art, such as site-directed mutagenesis or alanine-scanning mutagenesis (Cunningham and Wells, 1989, *Science* 244: 1081-1085). In the latter technique, single alanine mutations are introduced at every residue in the molecule, and the resultant mutant molecules are tested for [enzyme] activity to identify amino acid residues that are critical to the activity of the molecule. See also, Hilton et al., 1996, *J. Biol. Chem.* 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, *Science* 255: 306-312; Smith et al., 1992, *J. Mol. Biol.* 224: 899-904; Wlodaver et al., 1992, *FEBS Lett.* 309: 59-64. The identity of essential amino acids can also be inferred from an alignment with a related polypeptide.

Thus, the variant of the present invention may comprise further modifications, such as substitutions, insertions and/or deletions. Variants of the present invention may comprise such further modifications in order to obtain a variant having an improved performance, such as improved wash performance, improved liquefaction properties, and improved desizing properties.

In one embodiment, the number of further modifications in the variants of the present invention is 1 to 30, e.g. 1 to 20, e.g., 1 to 10 and 1 to 5, such as 1, 2, 3, 4, 5, 6, 7, 8, 9 or 10 modifications.

Thus, in one embodiment, the number of modifications is 1 to 20, such as 1 to 10, such as 1 to 5, such as 1, 2, 3, 4, 5, 6, 7, 8, 9, or 10 modifications.

It is believed that the variant of the present invention may be further stabilized and/or performance enhanced by further modifications. Specific modification may be relevant for the stability of the variants of the present invention. In a particular embodiment, the variant further comprises a substitution in at least one of the positions corresponding to Y242 and F266 wherein numbering is according to SEQ ID NO: 2.

In a particular embodiment, the substitution in position Y242 is Y242F and the substitution in position F266 is F266Y. In one embodiment, the variant comprises both the Y242F and the F266Y substitution. In a particular embodiment, the variant of the invention consists of besides the motif herein described either the substitution Y242F or F266Y, or both the substitutions Y242F and F266Y.

The variants of the present invention may further comprise at least one substitution in the positions corresponding to S243 and G475 of SEQ ID NO: 2. In particular, the substitutions may be S243Q and G475K. Thus, in one embodiment, the variant of the present invention comprises or consists of the following modifications:

T182*+G183*+Y242F+S243Q+F266Y+G475K,
S181*+T182*+Y242F+S243Q+F266Y+G475K,
R180*+T182*+Y242F+S243Q+F266Y+G475K, or
R180*+G183*+Y242F+S243Q+F266Y+G475K,
wherein numbering is according to SEQ ID NO: 2.

In one aspect, the parent alpha-amylase has a sequence identity to the polypeptide of SEQ ID NO: 1 of at least 89%, at least 90%, at least 91%, at least 92%, at least 93%, at least 94%, at least 95%, at least 96%, at least 97%, at least 98%, at least 99%, or 100%, which have alpha-amylase activity. In one aspect, the amino acid sequence of the parent alpha-amylase differs by up to 10 amino acids, e.g., 1, 2, 3, 4, 5, 6, 7, 8, 9, or 10, from the polypeptide of SEQ ID NO: 1.

In one aspect, the parent alpha-amylase has a sequence identity to the polypeptide of SEQ ID NO: 2 of at least 89%, at least 90%, at least 91%, at least 92%, at least 93%, at least 94%, at least 95%, at least 96%, at least 97%, at least 98%, at least 99%, or 100%, which have alpha-amylase activity. In one aspect, the amino acid sequence of the parent alpha-amylase differs by up to 10 amino acids, e.g., 1, 2, 3, 4, 5, 6, 7, 8, 9, or 10, from the polypeptide of SEQ ID NO: 2.

In one aspect, the parent alpha-amylase has a sequence identity to the polypeptide of SEQ ID NO: 3 of at least 89%, at least 90%, at least 91%, at least 92%, at least 93%, at least 94%, at least 95%, at least 96%, at least 97%, at least 98%, at least 99%, or 100%, which have alpha-amylase activity. In one aspect, the amino acid sequence of the parent alpha-amylase differs by up to 10 amino acids, e.g., 1, 2, 3, 4, 5, 6, 7, 8, 9, or 10, from the polypeptide of SEQ ID NO: 3.

In one aspect, the parent alpha-amylase comprises or consists of the amino acid sequence of SEQ ID NO: 1, 2, or 3.

In another aspect, the parent alpha-amylase comprises or consists of the amino acid sequence of SEQ ID NO: 1. In another aspect, the parent alpha-amylase comprises or consists of amino acids 1 to 485 of SEQ ID NO: 1.

In another aspect, the parent alpha-amylase is a fragment of the mature polypeptide of SEQ ID NO: 1 containing at least 100 amino acid residues, e.g., at least 200, at least 300, at least 400 and at least 450 amino acid residues.

In another embodiment, the parent alpha-amylase is an allelic variant of the polypeptide of SEQ ID NO: 1.

In another aspect, the parent alpha-amylase comprises or consists of the amino acid sequence of SEQ ID NO: 2. In another aspect, the parent alpha-amylase comprises or consists of amino acids 1 to 485 of SEQ ID NO: 2.

The parent alpha-amylase may be a fragment of the mature polypeptide of SEQ ID NO: 2 containing at least 100 amino acid residues, e.g., at least 200, at least 300, at least 400 and at least 450 amino acid residues.

The parent alpha-amylase may be an allelic variant of the polypeptide of SEQ ID NO: 2.

In another aspect, the parent alpha-amylase comprises or consists of the amino acid sequence of SEQ ID NO: 3. In another aspect, the parent alpha-amylase comprises or consists of amino acids 1 to 485 of SEQ ID NO: 3.

The parent alpha-amylase may be a fragment of the mature polypeptide of SEQ ID NO: 3 containing at least 100 amino acid residues, e.g., at least 200, at least 300, at least 400 and at least 450 amino acid residues.

The parent alpha-amylase may be an allelic variant of the polypeptide of SEQ ID NO: 3.

The polypeptide of SEQ ID NO: 1 or a fragment thereof may be used to design nucleic acid probes to identify and clone DNA encoding a parent alpha-amylase from strains of different genera or species according to methods well known in the art. In particular, such probes may be used for hybridization with the genomic DNA or cDNA of a cell of interest, following standard Southern blotting procedures, in order to identify and isolate the corresponding gene therein. Such probes may be considerably shorter than the entire sequence, but should be at least 15, e.g., at least 25, at least 35, or at least 70 nucleotides in length. Preferably, the nucleic acid probe is at least 100 nucleotides in length, e.g., at least 200 nucleotides, at least 300 nucleotides, at least 400 nucleotides, at least 500 nucleotides, at least 600 nucleotides, at least 700 nucleotides, at least 800 nucleotides, or at least 900 nucleotides in length. Both DNA and RNA probes can be used. The probes are typically labeled for detecting the corresponding gene (for example, with $^{32}P$, $^{3}H$, $^{35}S$, biotin, or avidin). Such probes are encompassed by the present invention.

A genomic DNA or cDNA library prepared from such other strains may be screened for DNA that hybridizes with the probes described above and encodes a parent. Genomic or other DNA from such other strains may be separated by agarose or polyacrylamide gel electrophoresis, or other separation techniques. DNA from the libraries or the separated DNA may be transferred to and immobilized on nitrocellulose or other suitable carrier material. In order to identify a clone or DNA that hybridizes with SEQ ID NO: 1 or a subsequence thereof, the carrier material is used in a Southern blot.

The polypeptide may be a hybrid polypeptide in which a region of one polypeptide is fused at the N-terminus or the C-terminus of a region of another polypeptide.

The parent may be a fusion polypeptide or cleavable fusion polypeptide in which another polypeptide is fused at the N-terminus or the C-terminus of the polypeptide of the present invention. A fusion polypeptide is produced by fusing a polynucleotide encoding another polypeptide to a polynucleotide of the present invention. Techniques for producing fusion polypeptides are known in the art, and include ligating the coding sequences encoding the polypeptides so that they are in frame and that expression of the fusion polypeptide is under control of the same promoter(s) and terminator. Fusion polypeptides may also be constructed using intein technology in which fusion polypeptides are created post-translationally (Cooper et al., 1993, *EMBO J.* 12: 2575-2583; Dawson et al., 1994, *Science* 266: 776-779).

A fusion polypeptide may further comprise a cleavage site between the two polypeptides. Upon secretion of the fusion protein, the site is cleaved releasing the two polypeptides. Examples of cleavage sites include, but are not limited to, the sites disclosed in Martin et al., 2003, *J. Ind. Microbiol. Biotechnol.* 3: 568-576; Svetina et al., 2000, *J. Biotechnol.* 76: 245-251; Rasmussen-Wilson et al., 1997, *Appl. Environ. Microbiol.* 63: 3488-3493; Ward et al., 1995, *Biotechnology* 13: 498-503; and Contreras et al., 1991, *Biotechnology* 9: 378-381; Eaton et al., 1986, *Biochemistry* 25: 505-512; Collins-Racie et al., 1995, *Biotechnology* 13: 982-987; Carter et al., 1989, *Proteins: Structure, Function, and Genetics* 6: 240-248; and Stevens, 2003, *Drug Discovery World* 4: 35-48.

The parent alpha-amylase may be obtained from microorganisms of any genus. For purposes of the present invention, the term "obtained from" as used herein in connection with a given source shall mean that the parent encoded by a polynucleotide is produced by the source or by a strain in which the polynucleotide from the source has been inserted. In one aspect, the parent is secreted extracellularly.

The parent may be a bacterial alpha-amylase. For example, the parent may be a Gram-positive bacterial polypeptide such as a *Bacillus* alpha-amylase.

In one aspect, the parent is a *Bacillus* sp. TS-23 alpha-amylase e.g., the alpha-amylase of SEQ ID NO: 1, 2, or 3.

The alpha-amylases of SEQ ID NO: 1, 2, and 3 as well as the variants hereof may be artificially manufactured by methods known in the art.

In one aspect, the variant has at least 89%, such as at least 90%, at least 91%, at least 92%, at least 93%, at least 94%, at least 95% identity, at least 96%, at least 97%, at least 98%, or at least 99%, but less than 100%, sequence identity to the amino acid sequence of the parent alpha-amylase.

The variant of the present invention may have at least 89% sequence identity to the amino acid sequence of the parent alpha-amylase and comprises a number of modifications, such as 1 to 20 modifications, such as 1, 2, 3, 4, 5, 6, 7, 8, 9, 10, 11, 12, 13, 14, 15, 16, 17, 18, 19, or 20. In particular, the number of modifications may be 1 to 10, such as 1, 2, 3, 4, 5, 6, 7, 8, 9, or 10 modifications. The number of modifications may be 1 to 5, such as 1, 2, 3, 4, or 5 modifications.

As can be seen from the Examples, the variants of the present invention have shown to have an improved property compared to the parent alpha-amylase.

In one embodiment, the variant has an improved stability, such as storage stability, thermo-stability, stability in detergents, and chelator stability, relative to said parent alpha-amylase.

In an embodiment, the variant has improved chemical stability compared to the parent alpha-amylase.

The term "chemical stability" as used herein, refers to the stability of the alpha-amylase variant or parent when the alpha-amylase variant or parent is in a composition comprising a chemical component. The chemical stability may be determined in a similar manner as shown in the Examples, i.e. incubate the alpha-amylase variant or parent in a composition comprising a chemical component at a specific temperature, e.g. 40 degrees Celsius for a given period of time, e.g. 4 hours, and then determine the residual activity by use of an alpha-amylase activity assay.

In an embodiment, the variant has improved oxidation stability compared to the parent alpha-amylase.

The term "oxidation stability" as used herein, refers to the stability of the alpha-amylase variant or parent when the alpha-amylase variant or parent is in a composition comprising a oxidizing component. The oxidation stability may be determined in a similar manner as shown in the Examples, i.e. incubate the alpha-amylase variant or parent in a composition comprising a oxidizing component at a specific temperature, e.g. 40 degrees Celsius for a given period of time, e.g. 4 hours, and then determine the residual activity by use of an alpha-amylase activity assay.

In an embodiment, the variant has improved pH stability compared to the parent alpha-amylase.

The term "pH stability" as used herein, refers to the stability of the alpha-amylase variant or parent when the alpha-amylase variant or parent is in a composition having an altered pH than what may be the optimal pH for the alpha-amylase. The pH stability may be determined in a similar manner as shown in the Examples, i.e. incubate the alpha-amylase variant or parent in a composition having an altered pH profile than what may be the natural pH for the alpha-amylase at a specific temperature, e.g. 40 degrees Celsius for a given period of time, e.g. 4 hours, and then determine the residual activity by use of an alpha-amylase activity assay.

In an embodiment, the variant has improved specific activity compared to the parent alpha-amylase.

The term "specific activity" as used herein, refers to the activity of the alpha-amylase variant or parent which is determined by use of an alpha-amylase specific activity assay as described in the Examples.

In an embodiment, the variant has improved stability under storage conditions compared to the parent alpha-amylase.

The term "storage stability" and "stability under storage conditions" as used herein, refers to the stability of the alpha-amylase variant or parent when the alpha-amylase variant or parent is in a formulation. The storage stability may be determined in a similar manner as shown in the Examples, i.e. incubate the alpha-amylase variant or parent in a composition at a specific temperature, e.g. 25 degrees Celsius for a given period of time, e.g. 2 hours, and then determine the residual activity by use of an alpha-amylase activity assay.

In an embodiment, the variant has improved substrate stability compared to the parent alpha-amylase.

The term "substrate stability" as used herein, refers to the stability of the alpha-amylase variant or parent alpha-amylase when the alpha-amylase variant or parent alpha-amylase is in a composition, such as detergent composition. The substrate stability may be determined in a similar manner as shown in the Examples, i.e. incubate the alpha-amylase variant or parent in a composition at a specific temperature, e.g. 60 degrees Celsius for a given period of time, e.g. 2 hours, and then determine the residual activity by use of an alpha-amylase activity assay.

In an embodiment, the variant has improved thermal activity compared to the parent alpha-amylase.

The term "thermal activity" as used herein, refers to the activity of the alpha-amylase variant or parent alpha-amylase when the alpha-amylase variant or parent alpha-amylase has been exposed to e.g. thermal stress or thermal changes. The thermal activity may be determined in a similar manner as shown in the Examples, i.e. incubate the alpha-amylase variant or parent at an elevated temperature, e.g. 60 degrees Celsius for a given period of time, e.g. 2 hours, and then determine the residual activity by use of an alpha-amylase activity assay.

In an embodiment, the variant has improved thermo-stability compared to the parent alpha-amylase.

The term "thermo-stability" as used herein, refers to the stability of the alpha-amylase variant or parent when the alpha-amylase variant or parent is tested or left at a specific high temperature, such as 60 degrees Celsius. The thermo-stability may be determined in a similar manner as shown in the Examples, i.e. incubate the alpha-amylase variant or parent in a composition at an elevated temperature, e.g. 60 degrees Celsius for a given period of time, e.g. 24 hours, and then determine the residual activity by use of an alpha-amylase activity assay.

In one embodiment, the variant has improved stability in detergents compared to the parent alpha-amylase.

The term "stability in detergents" as used herein, refers to the stability of the alpha-amylase variant or parent when the alpha-amylase variant or parent is in a detergent composition or formulation. The stability may be determined in a similar manner as shown in the Examples, i.e. incubate the alpha-amylase variant or parent in a detergent composition at a specific temperature, e.g. 25 degrees Celsius for a given period of time, e.g. 2 hours, and then determine the residual activity by use of an alpha-amylase activity assay.

In one embodiment, the variant has improved chelator stability compared to the parent alpha-amylase.

Thus, in one embodiment, the variant has an improved stability wherein the stability is determined by a Phadebas assay. Accordingly, the improved stability may be determined by an assay comprising the steps of diluting the variant in 100 mM Britton-Robinson buffer, and measuring the resulting blue solution by spectrophotometry at 620 nm.

Preparation of Variants of the Invention

The present invention also relates to methods for obtaining a variant having alpha-amylase activity, comprising introducing into a parent alpha-amylase a deletion of two amino acids selected from the positions corresponding to R180, S181, T182, and G183 of the amino acid sequence of SEQ ID NO: 1 providing an amino acid motif of FX1X2K (SEQ ID NO: 4), wherein X1 is R or S; and X2 may be selected from A, R, N, D, C, E, Q, G, H, I, L, K, M, F, P, S, T, W, Y, and V with the proviso that when X1 is R, then X2 is not S, said variant has an improved Residual Activity (RA) compared to an amylase comprising the motif FRSK (SEQ ID NO: 7), and wherein said variant has alpha-amylase activity; and recovering the variant.

The variants may be prepared using any mutagenesis procedure known in the art, such as site-directed mutagenesis, synthetic gene construction, semi-synthetic gene construction, random mutagenesis, shuffling, etc.

Site-directed mutagenesis is a technique in which one or more (e.g., several) mutations are introduced at one or more defined sites in a polynucleotide encoding the parent alpha-amylase.

Site-directed mutagenesis may be accomplished in vitro by PCR involving the use of oligonucleotide primers containing the desired mutation. Site-directed mutagenesis may also be performed in vitro by cassette mutagenesis involving the cleavage by a restriction enzyme at a site in the plasmid comprising a polynucleotide encoding the parent alpha-amylase and subsequent ligation of an oligonucleotide containing the mutation in the polynucleotide. Usually the restriction enzyme that digests the plasmid and the oligonucleotide is the same, permitting sticky ends of the plasmid and the insert to ligate to one another. See, e.g., Scherer and Davis, 1979, *Proc. Natl. Acad. Sci. USA* 76: 4949-4955; and Barton et al., 1990, *Nucleic Acids Res.* 18: 7349-4966.

Site-directed mutagenesis may also be accomplished in vivo by methods known in the art. See, e.g., U.S. Patent Application Publication No. 2004/0171154; Storici et al., 2001, *Nature Biotechnol.* 19: 773-776; Kren et al., 1998, *Nat. Med.* 4: 285-290; and Calissano and Macino, 1996, *Fungal Genet. Newslett.* 43: 15-16.

Any site-directed mutagenesis procedure may be used in the present invention. There are many commercial kits available that can be used to prepare variants.

Synthetic gene construction entails in vitro synthesis of a designed polynucleotide molecule to encode a polypeptide of interest. Gene synthesis may be performed utilizing a number of techniques, such as the multiplex microchip-based technology described by Tian et al. (2004, *Nature* 432: 1050-1054) and similar technologies wherein oligonucleotides are synthesized and assembled upon photo-programmable microfluidic chips.

Single or multiple amino acid substitutions, deletions, and/or insertions may be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156; WO 95/17413; or WO 95/22625. Other methods that may be used include error-prone PCR, phage display (e.g., Lowman et al., 1991, *Biochemistry* 30: 10832-10837; U.S. Pat. No. 5,223,409; WO 92/06204) and region-directed mutagenesis (Derbyshire et al., 1986, *Gene* 46: 145; Ner et al., 1988, *DNA* 7: 127).

Mutagenesis/shuffling methods may be combined with high-throughput, automated screening methods to detect activity of cloned, mutagenized polypeptides expressed by host cells (Ness et al., 1999, *Nature Biotechnology* 17: 893-896). Mutagenized DNA molecules that encode active polypeptides may be recovered from the host cells and rapidly sequenced using standard methods in the art. These methods allow the rapid determination of the importance of individual amino acid residues in a polypeptide.

Semi-synthetic gene construction is accomplished by combining aspects of synthetic gene construction, and/or site-directed mutagenesis, and/or random mutagenesis, and/or shuffling. Semi-synthetic construction is typified by a process utilizing polynucleotide fragments that are synthesized, in combination with PCR techniques. Defined regions of genes may thus be synthesized de novo, while other regions may be amplified using site-specific mutagenic primers, while yet other regions may be subjected to error-prone PCR or non-error prone PCR amplification. Polynucleotide subsequences may then be shuffled.

Polynucleotides

The present invention also relates to isolated polynucleotides encoding a variant of the present invention. Accordingly, the present invention relates to a polynucleotide encoding a variant which has alpha-amylase activity and has at least 89% sequence identity to SEQ ID NO: 1, wherein said variant comprises an amino acid motif of FX1X2K (SEQ ID NO: 4) at positions corresponding to amino acids 180 to 183 of SEQ ID NO: 2; wherein X1 is R or S; and X2 may be selected from A, R, N, D, C, E, Q, G, H, I, L, K, M, F, P, S, T, W, Y, and V with the proviso that when X1 is R, then X2 is not S, said variant has an improved Residual Activity (RA) compared to an amylase comprising the motif FRSK (SEQ ID NO: 7).

Nucleic Acid Constructs

The present invention relates to nucleic acid constructs comprising a polynucleotide encoding a variant of the present invention. Thus, the present invention relates to a nucleic acid construct comprising a polynucleotide encoding a variant which has alpha-amylase activity and has at least 89% sequence identity to SEQ ID NO: 1, wherein said variant comprises an amino acid motif of FX1X2K (SEQ ID NO: 4) at positions corresponding to amino acids 180 to 183 of SEQ ID NO: 2; wherein X1 is R or S; and X2 may be selected from A, R, N, D, C, E, Q, G, H, I, L, K, M, F, P, S, T, W, Y, and V with the proviso that when X1 is R, then X2 is not S, said variant has an improved Residual Activity (RA) compared to an amylase comprising the motif FRSK (SEQ ID NO: 7).

The present invention also relates to nucleic acid constructs comprising a polynucleotide encoding a variant of the present invention operably linked to one or more control sequences that direct the expression of the coding sequence in a suitable host cell under conditions compatible with the control sequences. Accordingly, the present invention relates to a nucleic acid construct comprising a polynucleotide encoding a variant which has alpha-amylase activity and has at least 89% sequence identity to SEQ ID NO: 1, wherein said variant comprises an amino acid motif of FX1X2K (SEQ ID NO: 4) at positions corresponding to amino acids 180 to 183 of SEQ ID NO: 2; wherein X1 is R or S; and X2 may be selected from A, R, N, D, C, E, Q, G, H, I, L, K, M, F, P, S, T, W, Y, and V with the proviso that when X1 is R, then X2 is not S, said variant has an improved Residual Activity (RA) compared to an amylase comprising the motif FRSK (SEQ ID NO: 7), wherein the polynucleotide is operably linked to one or more control sequences that direct the expression of the coding sequence in a suitable host cell under conditions compatible with the control sequences.

The polynucleotide may be manipulated in a variety of ways to provide for expression of a variant. Manipulation of the polynucleotide prior to its insertion into a vector may be desirable or necessary depending on the expression vector. The techniques for modifying polynucleotides utilizing recombinant DNA methods are well known in the art.

The control sequence may be a promoter, a polynucleotide which is recognized by a host cell for expression of the polynucleotide. The promoter contains transcriptional control sequences that mediate the expression of the variant. The promoter may be any polynucleotide that shows transcriptional activity in the host cell including mutant, truncated, and hybrid promoters, and may be obtained from genes encoding extracellular or intracellular polypeptides either homologous or heterologous to the host cell.

Examples of suitable promoters for directing transcription of the nucleic acid constructs of the present invention in a bacterial host cell are the promoters obtained from the Bacillus amyloliquefaciens alpha-alpha-amylase gene (amyQ), Bacillus licheniformis alpha-alpha-amylase gene (amyL), Bacillus licheniformis penicillinase gene (penP), Bacillus stearothermophilus maltogenic alpha-amylase gene (amyM), Bacillus subtilis levansucrase gene (sacB), Bacillus subtilis xylA and xylB genes, Bacillus thuringiensis cryIIIA gene (Agaisse and Lereclus, 1994, *Molecular Microbiology* 13: 97-107), *E. coli* lac operon, *E. coli* trc promoter (Egon et al., 1988, *Gene* 69: 301-315), *Streptomyces coelicolor* agarase gene (dagA), and prokaryotic beta-lactamase gene (Villa-Kamaroff et al., 1978, *Proc. Natl. Acad. Sci. USA* 75: 3727-3731), as well as the tac promoter (DeBoer et al., 1983, *Proc. Natl. Acad. Sci. USA* 80: 21-25). Further promoters are described in "Useful proteins from recombinant bacteria" in Gilbert et al., 1980, *Scientific American* 242: 74-94; and in Sambrook et al., 1989, supra. Examples of tandem promoters are disclosed in WO 99/43835.

Examples of suitable promoters for directing transcription of the nucleic acid constructs of the present invention in a filamentous fungal host cell are promoters obtained from the genes for *Aspergillus nidulans* acetamidase, *Aspergillus niger* neutral alpha-alpha-amylase, *Aspergillus niger* acid stable alpha-alpha-amylase, *Aspergillus niger* or *Aspergillus awamori* glucoalpha-amylase (glaA), *Aspergillus oryzae* TAKA alpha-amylase, *Aspergillus oryzae* alkaline protease, *Aspergillus oryzae* triose phosphate isomerase, *Fusarium oxysporum* trypsin-like protease (WO 96/00787), *Fusarium venenatum* amyloglucosidase (WO 00/56900), *Fusarium venenatum* Daria (WO 00/56900), *Fusarium venenatum* Quinn (WO 00/56900), *Rhizomucor miehei* lipase, *Rhizomucor miehei* aspartic proteinase, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase IV, *Trichoderma reesei* endoglucanase V, *Trichoderma reesei* xylanase I, *Trichoderma reesei* xylanase II, *Trichoderma reesei* beta-xylosidase, as well as the NA2-tpi promoter (a modified promoter from an *Aspergillus* neutral alpha-alpha-amylase gene in which the untranslated leader has been replaced by an untranslated leader from an *Aspergillus* triose phosphate isomerase gene; non-limiting examples include modified promoters from an *Aspergillus niger* neutral alpha-alpha-amylase gene in which the untranslated leader has been replaced by an untranslated leader from an *Aspergillus nidulans* or *Aspergillus oryzae* triose phosphate isomerase gene); and mutant, truncated, and hybrid promoters thereof.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae* 3-phosphoglycerate kinase. Other useful promoters for yeast host cells are described by Romanos et al., 1992, *Yeast* 8: 423-488.

The control sequence may also be a transcription terminator, which is recognized by a host cell to terminate transcription. The terminator sequence is operably linked to the 3'-terminus of the polynucleotide encoding the variant. Any terminator that is functional in the host cell may be used.

Preferred terminators for bacterial host cells are obtained from the genes for *Bacillus clausii* alkaline protease (aprH), *Bacillus licheniformis* alpha-alpha-amylase (amyL), and *Escherichia coli* ribosomal RNA (rrnB).

Preferred terminators for filamentous fungal host cells are obtained from the genes for *Aspergillus nidulans* anthranilate synthase, *Aspergillus niger* glucoalpha-amylase, *Aspergillus niger* alpha-glucosidase, *Aspergillus oryzae* TAKA alpha-amylase, and *Fusarium oxysporum* trypsin-like protease.

Preferred terminators for yeast host cells may be obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be an mRNA stabilizer region downstream of a promotor and upstream of the coding sequence of a gene which increases expression of the gene.

Examples of suitable mRNA stabilizer regions are obtained from a *Bacillus thuringiensis* cryIIIA gene (WO 94/25612) and a *Bacillus subtilis* SP82 gene (Hue et al., 1995, *Journal of Bacteriology* 177: 3465-3471).

The control sequence may also be a leader, a non-translated region of an mRNA that is important for translation by the host cell. The leader sequence is operably linked to the 5'-terminus of the polynucleotide encoding the variant. Any leader that is functional in the host cell may be used.

Preferred leaders for filamentous fungal host cells may be obtained from the genes for *Aspergillus oryzae* TAKA alpha-amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3'-terminus of the variant-encoding sequence and, when transcribed, is recognized by the host cell as a signal to add polyadenosine residues to transcribed mRNA. Any polyadenylation sequence that is functional in the host cell may be used.

Preferred polyadenylation sequences for filamentous fungal host cells may be obtained from the genes for *Aspergillus nidulans* anthranilate synthase, *Aspergillus niger* glucoalpha-amylase, *Aspergillus niger* alpha-glucosidase, *Aspergillus oryzae* TAKA alpha-amylase, and *Fusarium oxysporum* trypsin-like protease.

Useful polyadenylation sequences for yeast host cells are described by Guo and Sherman, 1995, *Mol. Cellular Biol.* 15: 5983-5990.

The control sequence may also be a signal peptide coding region that encodes a signal peptide linked to the N-terminus of a variant and directs the variant into the cell's secretory pathway. The 5'-end of the coding sequence of the polynucleotide may inherently contain a signal peptide coding sequence naturally linked in translation reading frame with the segment of the coding sequence that encodes the variant. Alternatively, the 5'-end of the coding sequence may contain a signal peptide coding sequence that is foreign to the coding sequence. A foreign signal peptide coding sequence may be required where the coding sequence does not naturally contain a signal peptide coding sequence. Alternatively, a foreign signal peptide coding sequence may simply replace the natural signal peptide coding sequence in order to enhance secretion of the variant. However, any signal peptide coding sequence that directs the expressed variant into the secretory pathway of a host cell may be used.

Effective signal peptide coding sequences for bacterial host cells are the signal peptide coding sequences obtained from the genes for *Bacillus* NCIB 11837 maltogenic alpha-amylase, *Bacillus licheniformis* subtilisin, *Bacillus licheniformis* beta-lactamase, *Bacillus stearothermophilus* alpha-amylase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109-137.

Effective signal peptide coding sequences for filamentous fungal host cells are the signal peptide coding sequences obtained from the genes for *Aspergillus niger* neutral alpha-amylase, *Aspergillus niger* glucoalpha-amylase, *Aspergillus oryzae* TAKA alpha-amylase, *Humicola insolens* cellulase, *Humicola insolens* endoglucanase V, *Humicola lanuginosa* lipase, and *Rhizomucor miehei* aspartic proteinase.

Useful signal peptides for yeast host cells may be obtained from the genes for *Saccharomyces cerevisiae* alpha-factor and *Saccharomyces cerevisiae* invertase. Other useful signal peptide coding sequences are described by Romanos et al., 1992, supra.

The control sequence may also be a propeptide coding sequence that encodes a propeptide positioned at the N-terminus of a variant. The resultant polypeptide is known as a proenzyme or propolypeptide (or a zymogen in some cases). A propolypeptide is generally inactive and can be converted to an active polypeptide by catalytic or autocatalytic cleavage of the propeptide from the propolypeptide. The propeptide coding sequence may be obtained from the genes for *Bacillus subtilis* alkaline protease (aprE), *Bacillus subtilis* neutral protease (nprT), *Myceliophthora thermophila* laccase (WO 95/33836), *Rhizomucor miehei* aspartic proteinase, and *Saccharomyces cerevisiae* alpha-factor.

Where both signal peptide and pro-peptide sequences are present, the pro-peptide sequence is positioned next to the N-terminus of the variant and the signal peptide sequence is positioned next to the N-terminus of the pro-peptide sequence.

It may also be desirable to add regulatory sequences that regulate expression of the variant relative to the growth of the host cell. Examples of regulatory systems are those that cause expression of the gene to be turned on or off in response to a chemical or physical stimulus, including the presence of a regulatory compound. Regulatory systems in prokaryotic systems include the lac, tac, and trp operator systems. In yeast, the ADH2 system or GAL1 system may be used. In filamentous fungi, the *Aspergillus niger* glucoalpha-amylase promoter, *Aspergillus oryzae* TAKA alpha-alpha-amylase promoter, and *Aspergillus oryzae* glucoalpha-amylase promoter may be used. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the polynucleotide encoding the variant would be operably linked with the regulatory sequence.

Expression Vectors

The present invention relates to expression vectors comprising a polynucleotide of the invention. Thus, the present invention relates to an expression vector comprising a polynucleotide encoding a variant which has alpha-amylase activity and has at least 89% sequence identity to SEQ ID NO: 1, wherein said variant comprises an amino acid motif of FX1X2K (SEQ ID NO: 4) at positions corresponding to amino acids 180 to 183 of SEQ ID NO: 2; wherein X1 is R or S; and X2 may be selected from A, R, N, D, C, E, Q, G, H, I, L, K, M, F, P, S, T, W, Y, and V with the proviso that when X1 is R, then X2 is not S, said variant has an improved Residual Activity (RA) compared to an amylase comprising the motif FRSK (SEQ ID NO: 7).

The present invention also relates to recombinant expression vectors comprising a polynucleotide encoding a variant of the present invention, a promotor, and transcriptional and translational stop signals. Accordingly, the present invention relates to expression vectors comprising a polynucleotide encoding a variant which has alpha-amylase activity and has at least 89% sequence identity to SEQ ID NO: 1, wherein said variant comprises an amino acid motif of FX1X2K (SEQ ID NO: 4) at positions corresponding to amino acids 180 to 183 of SEQ ID NO: 2; wherein X1 is R or S; and X2 may be selected from A, R, N, D, C, E, Q, G, H, I, L, K, M, F, P, S, T, W, Y, and V with the proviso that when X1 is R, then X2 is not S, said variant has an improved Residual Activity (RA) compared to an amylase comprising the motif FRSK (SEQ ID NO: 7); a promotor, and transcriptional and translational stop signals.

The various nucleotide and control sequences may be joined together to produce a recombinant expression vector that may include one or more convenient restriction sites to allow for insertion or substitution of the polynucleotide encoding the variant at such sites. Alternatively, the polynucleotide may be expressed by inserting the polynucleotide or a nucleic acid construct comprising the polynucleotide into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may comprise any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector preferably comprises one or more selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are *Bacillus licheniformis* or *Bacillus subtilis* dal genes, or markers that confer antibiotic resistance such as ampicillin, chloramphenicol, kanamycin, neomycin, spectinomycin or tetracycline resistance. Suitable markers for yeast host cells include, but are not limited to, ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are *Aspergillus nidulans* or *Aspergillus oryzae* amdS and pyrG genes and a *Streptomyces hygroscopicus* bar gene.

The vector preferably comprises an element(s) that permits integration of the vector into the host cell's genome or autonomous replication of the vector in the cell independent of the genome.

For integration into the host cell genome, the vector may rely on the polynucleotide's sequence encoding the variant or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMβ1 permitting replication in *Bacillus*.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANSI (Gems et al., 1991, *Gene* 98: 61-67; Cullen et al., 1987, *Nucleic Acids Res.* 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into a host cell to increase production of a variant. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, may be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention relates to host cells comprising a polynucleotide according to the invention. Thus, the present invention relates to a host cell comprising a polynucleotide encoding a variant which has alpha-amylase activity and has at least 89% sequence identity to SEQ ID NO: 1, wherein said variant comprises an amino acid motif of FX1X2K (SEQ ID NO: 4) at positions corresponding to amino acids 180 to 183 of SEQ ID NO: 2; wherein X1 is R or S; and X2 may be selected from A, R, N, D, C, E, Q, G, H, I, L, K, M, F, P, S, T, W, Y, and V with the proviso that when X1 is R, then X2 is not S, said variant has an improved Residual Activity (RA) compared to an amylase comprising the motif FRSK (SEQ ID NO: 7).

The invention also relates to recombinant host cells, comprising a polynucleotide encoding a variant of the present invention operably linked to one or more control sequences that direct the production of the variant of the present invention. Accordingly, the present invention relates to host cells, comprising a polynucleotide encoding a variant which has alpha-amylase activity and has at least 89% sequence identity to SEQ ID NO: 1, wherein said variant comprises an amino acid motif of FX1X2K (SEQ ID NO: 4) at positions corresponding to amino acids 180 to 183 of SEQ ID NO: 2; wherein X1 is R or S; and X2 may be selected from A, R, N, D, C, E, Q, G, H, I, L, K, M, F, P, S, T, W, Y, and V with the proviso that when X1 is R, then X2 is not S, said variant has an improved Residual Activity (RA) compared to an amylase comprising the motif FRSK (SEQ ID NO: 7), wherein the polynucleotide is operably linked to one or more control sequences that direct the production of the variant.

A construct or vector comprising a polynucleotide is introduced into a host cell so that the construct or vector is maintained as a chromosomal integrant or as a self-replicating extrachromosomal vector as described earlier. The term "host cell" encompasses any progeny of a parent cell that is not identical to the parent cell due to mutations that occur during replication. The choice of a host cell will to a large extent depend upon the gene encoding the variant and its source.

The host cell may be any cell useful in the recombinant production of a variant, e.g., a prokaryote or a eukaryote.

The prokaryotic host cell may be any Gram-positive or Gram-negative bacterium. Gram-positive bacteria include, but are not limited to, *Bacillus, Clostridium, Enterococcus, Geobacillus, Lactobacillus, Lactococcus, Oceanobacillus, Staphylococcus, Streptococcus,* and *Streptomyces*. Gram-negative bacteria include, but are not limited to, *Campylobacter, E. coli, Flavobacterium, Fusobacterium, Helicobacter, Ilyobacter, Neisseria, Pseudomonas, Salmonella,* and *Ureaplasma*.

The bacterial host cell may be any *Bacillus* cell including, but not limited to, *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis,* and *Bacillus thuringiensis* cells.

The bacterial host cell may also be any *Streptococcus* cell including, but not limited to, *Streptococcus equisimilis, Streptococcus pyogenes, Streptococcus uberis,* and *Streptococcus equi* subsp. *Zooepidemicus* cells.

The bacterial host cell may also be any *Streptomyces* cell, including, but not limited to, *Streptomyces achromogenes, Streptomyces avermitilis, Streptomyces coelicolor, Streptomyces griseus*, and *Streptomyces lividans* cells.

The introduction of DNA into a *Bacillus* cell may be effected by protoplast transformation (see, e.g., Chang and Cohen, 1979, *Mol. Gen. Genet.* 168: 111-115), competent cell transformation (see, e.g., Young and Spizizen, 1961, *J. Bacteriol.* 81: 823-829, or Dubnau and Davidoff-Abelson, 1971, *J. Mol. Biol.* 56: 209-221), electroporation (see, e.g., Shigekawa and Dower, 1988, *Biotechniques* 6: 742-751), or conjugation (see, e.g., Koehler and Thorne, 1987, *J. Bacteriol.* 169: 5271-5278). The introduction of DNA into an *E. coli* cell may be effected by protoplast transformation (see, e.g., Hanahan, 1983, *J. Mol. Biol.* 166: 557-580) or electroporation (see, e.g., Dower et al., 1988, *Nucleic Acids Res.* 16: 6127-6145). The introduction of DNA into a *Streptomyces* cell may be effected by protoplast transformation, electroporation (see, e.g., Gong et al., 2004, *Folia Microbiol.* (Praha) 49: 399-405), conjugation (see, e.g., Mazodier et al., 1989, *J. Bacteriol.* 171: 3583-3585), or transduction (see, e.g., Burke et al., 2001, *Proc. Natl. Acad. Sci. USA* 98: 6289-6294). The introduction of DNA into a *Pseudomonas* cell may be effected by electroporation (see, e.g., Choi et al., 2006, *J. Microbiol. Methods* 64: 391-397), or conjugation (see, e.g., Pinedo and Smets, 2005, *Appl. Environ. Microbiol.* 71: 51-57). The introduction of DNA into a *Streptococcus* cell may be effected by natural competence (see, e.g., Perry and Kuramitsu, 1981, *Infect. Immun.* 32: 1295-1297), protoplast transformation (see, e.g., Catt and Jollick, 1991, *Microbios* 68: 189-207), electroporation (see, e.g., Buckley et al., 1999, *Appl. Environ. Microbiol.* 65: 3800-3804) or conjugation (see, e.g., Clewell, 1981, *Microbiol. Rev.* 45: 409-436). However, any method known in the art for introducing DNA into a host cell can be used.

The host cell may also be a eukaryote, such as a mammalian, insect, or fungal cell.

The host cell may be a fungal cell. "Fungi" as used herein includes the phyla Ascomycota, Basidiomycota, Chytridiomycota, and Zygomycota as well as the Oomycota and all mitosporic fungi (as defined by Hawksworth et al., In, Ainsworth and Bisby's Dictionary of The Fungi, 8th edition, 1995, CAB International, University Press, Cambridge, UK).

The fungal host cell may be a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in Biology and Activities of Yeast (Skinner, Passmore, and Davenport, editors, *Soc. App. Bacteriol. Symposium Series* No. 9, 1980).

The yeast host cell may be a *Candida, Hansenula, Kluyveromyces, Pichia, Saccharomyces, Schizosaccharomyces*, or *Yarrowia* cell such as a *Kluyveromyces lactis, Saccharomyces carlsbergensis, Saccharomyces cerevisiae, Saccharomyces diastaticus, Saccharomyces douglasii, Saccharomyces kluyveri, Saccharomyces norbensis, Saccharomyces oviformis*, or *Yarrowia lipolytica* cell.

The fungal host cell may be a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

The filamentous fungal host cell may be an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes*, or *Trichoderma* cell.

For example, the filamentous fungal host cell may be an *Aspergillus awamori, Aspergillus foetidus, Aspergillus fumigatus, Aspergillus japonicus, Aspergillus nidulans, Aspergillus niger, Aspergillus oryzae, Bjerkandera adusta, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Coprinus cinereus, Coriolus hirsutus, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucormiehei, Myceliophthora thermophila, Neurospora crassa, Penicillium purpurogenum, Phanerochaete chrysosporium, Phlebia radiata, Pleurotus eryngii, Thielavia terrestris, Trametes villosa, Trametes versicolor, Trichoderma harzianum, Trichoderma koningii, Trichoderma longibrachiatum, Trichoderma reesei*, or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238023, Yelton et al., 1984, *Proc. Natl. Acad. Sci. USA* 81: 1470-1474, and Christensen et al., 1988, *Bio/Technology* 6: 1419-1422. Suitable methods for transforming *Fusarium* species are described by Malardier et al., 1989, *Gene* 78: 147-156, and WO 96/00787. Yeast may be transformed using the procedures described by Becker and Guarente, In Abelson, J. N. and Simon, M. I., editors, *Guide to Yeast Genetics and Molecular Biology, Methods in Enzymology*, Volume 194, pp 182-187, Academic Press, Inc., New York; Ito et al., 1983, *J. Bacteriol.* 153: 163; and Hinnen et al., 1978, *Proc. Natl. Acad. Sci. USA* 75: 1920.

Methods of Production

The present invention also relates to methods of producing a variant, comprising: (a) cultivating a host cell of the present invention under conditions suitable for expression of the variant; and (b) recovering the variant. Accordingly, the present invention relates to a method of producing a variant, comprising (a) cultivating a host cell comprising a polynucleotide encoding a variant which has alpha-amylase activity and has at least 89% sequence identity to SEQ ID NO: 1, wherein said variant comprises an amino acid motif of FX1X2K (SEQ ID NO: 4) at positions corresponding to amino acids 180 to 183 of SEQ ID NO: 2; wherein X1 is R or S; and X2 may be selected from A, R, N, D, C, E, Q, G, H, I, L, K, M, F, P, S, T, W, Y, and V with the proviso that when X1 is R, then X2 is not S, said variant has an improved Residual Activity (RA) compared to an amylase comprising the motif FRSK (SEQ ID NO: 7), under conditions suitable for expression of the variant; and (b) recovering the variant.

The host cells are cultivated in a nutrient medium suitable for production of the variant using methods known in the art. For example, the cell may be cultivated by shake flask cultivation, or small-scale or large-scale fermentation (including continuous, batch, fed-batch, or solid state fermentations) in laboratory or industrial fermentors performed in a suitable medium and under conditions allowing the variant to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the variant is secreted into the nutrient medium, the variant can be recovered directly from the medium. If the variant is not secreted, it can be recovered from cell lysates.

The variant may be detected using methods known in the art that are specific for the variants. These detection methods include, but are not limited to, use of specific antibodies, formation of an enzyme product, or disappearance of an enzyme substrate. For example, an enzyme assay may be used to determine the activity of the variant.

The variant may be recovered using methods known in the art. For example, the variant may be recovered from the nutrient medium by conventional procedures including, but not limited to, collection, centrifugation, filtration, extraction, spray-drying, evaporation, or precipitation.

The variant may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, Janson and Ryden, editors, VCH Publishers, New York, 1989) to obtain substantially pure variants.

In an alternative aspect, the variant is not recovered, but rather a host cell of the present invention expressing the variant is used as a source of the variant.

Compositions of the Invention

The present invention also relates to compositions comprising a variant of the present invention. Accordingly, the present invention relates to compositions comprising a variant which has alpha-amylase activity and has at least 89% sequence identity to SEQ ID NO: 1, wherein said variant comprises an amino acid motif of FX1X2K (SEQ ID NO: 4) at positions corresponding to amino acids 180 to 183 of SEQ ID NO: 2; wherein X1 is R or S; and X2 may be selected from A, R, N, D, C, E, Q, G, H, I, L, K, M, F, P, S, T, W, Y, and V with the proviso that when X1 is R, then X2 is not S, said variant has an improved Residual Activity (RA) compared to an amylase comprising the motif FRSK (SEQ ID NO: 7).

Preferably, the compositions are enriched in such a variant. The term "enriched" means that the alpha-amylase activity of the composition has been increased, e.g., with an enrichment factor of 1.1.

The composition may comprise a variant as the major enzymatic component, e.g., a mono-component composition. Alternatively, the composition may comprise multiple enzymatic activities, such as an aminopeptidase, amylase, carbohydrase, carboxypeptidase, catalase, cellulase, chitinase, cutinase, cyclodextrin glycosyltransferase, deoxyribonuclease, esterase, alpha-galactosidase, beta-galactosidase, glucoamylase, alpha-glucosidase, beta-glucosidase, haloperoxidase, invertase, laccase, lipase, mannosidase, oxidase, pectinolytic enzyme, peptidoglutaminase, peroxidase, phytase, polyphenoloxidase, proteolytic enzyme, ribonuclease, transglutaminase, or xylanase. The additional enzyme(s) may be produced, for example, by a microorganism belonging to the genus *Aspergillus*, e.g., *Aspergillus aculeatus, Aspergillus awamori, Aspergillus foetidus, Aspergillus fumigatus, Aspergillus japonicus, Aspergillus nidulans, Aspergillus niger,* or *Aspergillus oryzae; Fusarium,* e.g., *Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sulphureum, Fusarium toruloseum, Fusarium trichothecioides,* or *Fusarium venenatum; Humicola,* e.g., *Humicola insolens* or *Humicola lanuginosa;* or *Trichoderma,* e.g., *Trichoderma harzianum, Trichoderma koningii, Trichoderma longibrachiatum, Trichoderma reesei,* or *Trichoderma viride.*

The compositions may be prepared in accordance with methods known in the art and may be in the form of a liquid or a dry composition. For instance, the composition may be in the form of a granulate or a microgranulate. The variant may be stabilized in accordance with methods known in the art.

The detergent enzyme(s) may be included in a detergent composition by adding separate additives containing one or more enzymes, or by adding a combined additive comprising all of these enzymes. A detergent additive of the invention, i.e., a separate additive or a combined additive, can be formulated, e.g., granulate, a liquid, a slurry, etc. Preferred detergent additive formulations are granulates, in particular non-dusting granulates, liquids, in particular stabilized liquids, or slurries. Thus, the present invention also relates to a detergent additive comprising a variant of the invention, optionally in the form of a non-dusting granulate, stabilized liquid, or protected enzyme. Accordingly, the present invention relates to a detergent additive comprising a variant which has alpha-amylase activity and has at least 89% sequence identity to SEQ ID NO: 1, wherein said variant comprises an amino acid motif of FX1X2K (SEQ ID NO: 4) at positions corresponding to amino acids 180 to 183 of SEQ ID NO: 2; wherein X1 is R or S; and X2 may be selected from A, R, N, D, C, E, Q, G, H, I, L, K, M, F, P, S, T, W, Y, and V with the proviso that when X1 is R, then X2 is not S, said variant has an improved Residual Activity (RA) compared to an amylase comprising the motif FRSK (SEQ ID NO: 7), optionally, wherein the detergent additive is in the form of a non-dusting granulate, stabilized liquid, or protected enzyme.

In one aspect, the present invention relates to detergent compositions comprising a variant of the present invention in combination with one or more additional cleaning composition components. Accordingly, the present invention relates to a detergent composition comprising a variant which has alpha-amylase activity and has at least 89% sequence identity to SEQ ID NO: 1, wherein said variant comprises an amino acid motif of FX1X2K (SEQ ID NO: 4) at positions corresponding to amino acids 180 to 183 of SEQ ID NO: 2; wherein X1 is R or S; and X2 may be selected from A, R, N, D, C, E, Q, G, H, I, L, K, M, F, P, S, T, W, Y, and V with the proviso that when X1 is R, then X2 is not S, said variant has an improved Residual Activity (RA) compared to an amylase comprising the motif FRSK (SEQ ID NO: 7), in combination with one or more additional cleaning composition component.

The choice of additional components is within the skill of the artisan and includes conventional ingredients, including the exemplary non-limiting components set forth below.

The choice of components may include, for textile care, such as laundry, the consideration of the type of textile to be cleaned, the type and/or degree of soiling, the temperature at which cleaning is to take place, and the formulation of the detergent product. Although components mentioned below are categorized by general header according to a particular functionality, this is not to be construed as a limitation, as a component may comprise additional functionalities as will be appreciated by the skilled artisan.

Accordingly, the present invention also relates to a composition which is a cleaning composition.

A composition according to the present invention may further comprise a detergent component, such as a surfactant, builder, bleaching systems, bleach activator, polymers, and fabric hueing agents.

The detergent composition of the invention may for example be directed to an ADW (Automatic Dish Wash) composition comprising an enzyme of the present invention in combination with one or more additional ADW composition components. The choice of additional components is within the skill of the artisan and includes conventional ingredients, including the exemplary non-limiting components set forth below. Accordingly, in one aspect, the invention relates to a manual or automatic dishwashing detergent composition comprising a variant of the invention, and optionally a surfactant.

The detergent composition of the invention may for example be formulated as a hand or machine laundry detergent composition including a laundry additive composition suitable for pre-treatment of stained fabrics and a rinse added fabric softener composition, or be formulated as a detergent composition for use in general household hard surface cleaning operations, or be formulated for hand or machine dishwashing operations. Accordingly, in one aspect, the present invention relates to a manual or automatic laundry detergent composition comprising a variant according to the invention.

In a specific aspect, the invention provides a detergent concentrate/additive comprising the alpha-amylase polypeptide of the invention. The detergent additive, as well as the detergent composition, may comprise one or more other enzymes such as a protease, a lipase, a peroxidase, another amylolytic enzyme, e.g., another alpha-amylase, glucoamylase, maltogenic amylase, CGTase and/or a cellulase, mannanase (such as MANNAWAY™ from Novozymes, Denmark)), pectinase, pectine lyase, cutinase, and/or laccase.

In general, the properties of the chosen enzyme(s) should be compatible with the selected detergent, (i.e., pH-optimum, compatibility with other enzymatic and non-enzymatic ingredients, etc.), and the enzyme(s) should be present in effective amounts.

Proteases:

Suitable proteases include those of animal, vegetable or microbial origin. Microbial origin is preferred. Chemically modified or protein engineered mutants are included. The protease may be a serine protease or a metallo protease, preferably an alkaline microbial protease or a trypsin-like protease. Examples of alkaline proteases are subtilisins, especially those derived from Bacillus, e.g., subtilisin Novo, subtilisin Carlsberg, subtilisin 309, subtilisin 147 and subtilisin 168 (described in WO 89/06279). Examples of trypsin-like pro-teases are trypsin (e.g., of porcine or bovine origin) and the Fusarium protease described in WO 89/06270 and WO 94/25583.

Examples of useful proteases are the variants described in WO 92/19729, WO 98/20115, WO 98/20116, and WO 98/34946, especially the variants with substitutions in one or more of the following positions: 27, 36, 57, 76, 87, 97, 101, 104, 120, 123, 167, 170, 194, 206, 218, 222, 224, 235 and 274. Preferred commercially available protease enzymes include ALCALASE®, SAVINASE® (SEQ ID NO: 3), PRIMASE®, DURALASE®, ESPERASE®, and KANNASE® (from Novozymes A/S), MAXATASE®, MAXACAL, MAXAPEM®, PROPERASE®, PURAFECT®, PURAFECT OXP®, FN2®, FN3®, FN4® (Genencor International Inc.).

Lipases:

Suitable lipases include those of bacterial or fungal origin. Chemically modified or protein engineered mutants are included. Examples of useful lipases include lipases from Humicola (synonym Thermomyces), e.g., from H. lanuginosa (T. lanuginosus) as described in EP 258 068 and EP 305 216 or from H. insolens as described in WO 96/13580, a Pseudomonas lipase, e.g., from P. alcaligenes or P. pseudoalcaligenes (EP 218 272), P. cepacia (EP 331 376), P. stutzeri (GB 1,372,034), P. fluorescens, Pseudomonas sp. strain SD 705 (WO 95/06720 and WO 96/27002), P. wisconsinensis (WO 96/12012), a Bacillus lipase, e.g., from B. subtilis (Dartois et al. (1993), Biochemica et Biophysica Acta, 1131:253-360), B. stearothermophilus (JP 64/744992) or B. pumilus (WO 91/16422). Other examples are lipase variants such as those described in WO 92/05249, WO 94/01541, EP 407 225, EP 260 105, WO 95/35381, WO 96/00292, WO 95/30744, WO 94/25578, WO 95/14783, WO 95/22615, WO 97/04079 and WO 97/07202.

Preferred commercially available lipase enzymes include LIPOLASE™ and LIPOLASE ULTRA™ (Novozymes A/S).

Amylases:

Suitable amylases (alpha and/or beta) include those of bacterial or fungal origin. Chemically modified or protein engineered mutants are included. Amylases include, for example, alpha-amylases obtained from Bacillus, e.g., a special strain of B. licheniformis, described in more detail in GB 1,296,839. Examples of useful alpha-amylases are the variants described in WO 94/02597, WO 94/18314, WO 96/23873, and WO 97/43424, especially the variants with substitutions in one or more of the following positions: 15, 23, 105, 106, 124, 128, 133, 154, 156, 181, 188, 190, 197, 202, 208, 209, 243, 264, 304, 305, 391, 408, and 444. Commercially available alpha-amylases are DURAMYL™, LIQUEZYME™, TERMAMYL™, NATALASE™, Everest™, FUNGAMYL™ and BAN™, Amplify™, Amplify Prime™, Stainzyme™, Stainzyme Plus™ (Novozymes A/S), Preferenz S100, Preferenz S110, Preferenz S1000 (SEQ ID NO: 11), Excellenz S110, Excellenz S1000, Excellenz S2000, RAPIDASE™ and PURASTAR™ (from Genencor International Inc.).

Cellulases:

Suitable cellulases include those of bacterial or fungal origin. Chemically modified or protein engineered mutants are included. Suitable cellulases include cellulases from the genera Bacillus, Pseudomonas, Humicola, Fusarium, Thielavia, Acremonium, e.g., the fungal cellulases produced from Humicola insolens, Myceliophthora thermophila and Fusarium oxysporum disclosed in U.S. Pat. Nos. 4,435,307, 5,648,263, 5,691,178, 5,776,757 and WO 89/09259. Especially suitable cellulases are the alkaline or neutral cellulases having colour care benefits. Examples of such cellulases are cellulases described in EP 0 495 257, EP 0 531 372, WO 96/11262, WO 96/29397, WO 98/08940. Other examples are cellulase variants such as those described in WO 94/07998, EP 0 531 315, U.S. Pat. Nos. 5,457,046, 5,686,593, 5,763,254, WO 95/24471, WO 98/12307 and PCT/DK98/00299.

Commercially available cellulases include CELLUZYME®, and CAREZYME® (Novozymes A/S), CLAZINASE®, and PURADAX HA® (Genencor International Inc.), and KAC-500(B)® (Kao Corporation).

Peroxidases/Oxidases:

Suitable peroxidases/oxidases include those of plant, bacterial or fungal origin. Chemically modified or protein engineered mutants are included. Examples of useful peroxidases include peroxidases from *Coprinus*, e.g., from *C. cinereus*, and variants thereof as those described in WO 93/24618, WO 95/10602, and WO 98/15257. Commercially available peroxidases include GUARDZYME® (Novozymes A/S).

Lechinases/Beta-Glucanases:

Suitable Lechinases include those of bacterial or fungal origin. They may be chemically modified or protein engineered. Examples of useful beta-glucanases include those described in WO 2015/144824 (Novozymes A/S) and WO 99/06516 (Henkel KGAA).

The detergent enzyme(s) may be included in a detergent composition by adding separate additives containing one or more enzymes, or by adding a combined additive comprising all of these enzymes. A detergent additive of the invention, i.e., a separate additive or a combined additive, can be formulated, e.g., granulate, a liquid, a slurry, etc. Preferred detergent additive formulations are granulates, in particular non-dusting granulates, liquids, in particular stabilized liquids, or slurries.

Non-dusting granulates may be produced, e.g., as disclosed in U.S. Pat. Nos. 4,106,991 and 4,661,452 and may optionally be coated by methods known in the art. Examples of waxy coating materials are poly(ethylene oxide) products (polyethyleneglycol, PEG) with mean molar weights of 1000 to 20000; ethoxylated nonyl-phenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in GB 1483591. Liquid enzyme preparations may, for instance, be stabilized by adding a polyol such as propylene glycol, a sugar or sugar alcohol, lactic acid or boric acid according to established methods. Protected enzymes may be prepared according to the method disclosed in EP 238 216.

The detergent composition of the invention may be in any convenient form, e.g., a bar, a tablet, a powder, a granule, a paste or a liquid. A liquid detergent may be aqueous, typically containing up to 70% water and 0-30% organic solvent, or non-aqueous.

The detergent composition comprises one or more surfactants, which may be non-ionic including semi-polar and/or anionic and/or cationic and/or zwitterionic. The surfactants are typically present at a level of from 0.1% to 60% by weight.

When included therein the detergent will usually comprise from about 1% to about 40% of an anionic surfactant such as linear alkylbenzenesulfonate, alpha-olefinsulfonate, alkyl sulfate (fatty alcohol sulfate), alcohol ethoxysulfate, secondary alkanesulfonate, alpha-sulfo fatty acid methyl ester, alkyl- or alkenylsuccinic acid or soap.

When included therein the detergent will usually comprise from about 0.2% to about 40% of a non-ionic surfactant such as alcohol ethoxylate, nonyl-phenol ethoxylate, alkylpolyglycoside, alkyldimethylamine-oxide, ethoxylated fatty acid monoethanol-amide, fatty acid mono-ethanol-amide, polyhydroxy alkyl fatty acid amide, or N-acyl N-alkyl derivatives of glucosamine ("glucamides").

The detergent may comprise 0-65% of a detergent builder or complexing agent such as MGDA, GLDA, zeolite, diphosphate, tripho-sphate, phosphonate, carbonate, citrate, nitrilotriacetic acid, ethylenediaminetetraacetic acid, diethylenetri-aminepen-taacetic acid, alkyl- or alkenylsuccinic acid, soluble silicates or layered silicates (e.g. SKS-6 from Hoechst).

The detergent may comprise one or more polymers. Examples are carboxymethylcellulose, poly(vinyl-pyrrolidone), poly (ethylene glycol), poly(vinyl alcohol), poly (vinylpyridine-N-oxide), poly(vinylimidazole), polycarboxylates such as sulfonated polymers, polyacrylates, maleic/acrylic acid copolymers and lauryl methacrylate/acrylic acid co-polymers.

The detergent may contain a bleaching system, which may comprise a $H_2O_2$ source such as perborate or percarbonate which may be combined with a peracid-forming bleach activator such as bleach catalysts, e.g. Mn-based or Co-based, tetraacetylethylenediamine or nonanoyloxybenzenesul-fonate. Alternatively, the bleaching system may comprise peroxyacids of, e.g., the amide, imide, or sulfone type.

The enzyme(s) of the detergent composition of the invention may be stabilized using conventional stabilizing agents, e.g., a polyol such as propylene glycol or glycerol, a sugar or sugar alcohol, lactic acid, boric acid, or a boric acid derivative, e.g., an aromatic borate ester, or a phenyl boronic acid derivative such as 4-formylphenyl boronic acid, and the composition may be formulated as described in, e.g., WO 92/19709 and WO 92/19708.

The detergent may also contain other conventional detergent ingredients such as e.g. fabric conditioners including clays, foam boosters, suds suppressors, anti-corrosion agents, soil-suspending agents, anti-soil re-deposition agents, dyes, bactericides, optical brighteners, hydrotropes, tarnish inhibitors, or perfumes.

A hydrotrope is a compound that solubilises hydrophobic compounds in aqueous solutions (or oppositely, polar substances in a non-polar environment). Typically, hydrotropes have both hydrophilic and a hydrophobic character (so-called amphiphilic properties as known from surfactants); however, the molecular structure of hydrotropes generally do not favor spontaneous self-aggregation, see e.g. review by Hodgdon and Kaler (2007), Current Opinion in Colloid & Interface Science 12: 121-128. Hydrotropes do not display a critical concentration above which self-aggregation occurs as found for surfactants and lipids forming miceller, lamellar or other well defined meso-phases. Instead, many hydrotropes show a continuous-type aggregation process where the sizes of aggregates grow as concentration increases. However, many hydrotropes alter the phase behavior, stability, and colloidal properties of systems containing substances of polar and non-polar character, including mixtures of water, oil, surfactants, and polymers. Hydrotropes are classically used across industries from pharma, personal care, food, to technical applications. Use of hydrotropes in detergent compositions allow for example more concentrated formulations of surfactants (as in the process of compacting liquid detergents by removing water) without inducing undesired phenomena such as phase separation or high viscosity.

The detergent composition may comprise about 0-65% by weight, such as about 5% to about 50% of a detergent builder or co-builder, or a mixture thereof. In a dish wash detergent, the level of builder is typically 40-65%, particularly 50-65%. The builder and/or co-builder may particularly be a chelating agent that forms water-soluble complexes with Ca and Mg. Any builder and/or co-builder known in the art for use in laundry/ADW/hard surface cleaning detergents may be utilized. Non-limiting examples of builders include zeolites, diphosphates (pyrophosphates), triphosphates such as sodium triphosphate (STP or STPP), carbonates such as sodium carbonate, soluble silicates such as sodium metasilicate, layered silicates (e.g., SKS-6 from Hoechst), ethanolamines such as 2-aminoethan-1-ol (MEA), diethanolamine (DEA, also known as 2,2'-iminodiethan-1-ol), triethanolamine (TEA, also known as 2,2',2''-nitrilotriethan-1-ol), and (carboxymethyl)inulin (CMI), and combinations thereof.

The detergent may comprise 0-30% by weight, such as about 1% to about 20%, of a bleaching system. Any bleaching system known in the art for use in laundry/ADW/hard surface cleaning detergents may be utilized. Suitable bleaching system components include bleaching catalysts, photobleaches, bleach activators, sources of hydrogen peroxide such as sodium percarbonate, sodium perborates and hydrogen peroxide—urea (1:1), preformed peracids and mixtures thereof. Suitable preformed peracids include, but are not limited to, peroxycarboxylic acids and salts, diperoxydicarboxylic acids, perimidic acids and salts, peroxymonosulfuric acids and salts, for example, Oxone (R), and mixtures thereof. Non-limiting examples of bleaching systems include peroxide-based bleaching systems, which may comprise, for example, an inorganic salt, including alkali metal salts such as sodium salts of perborate (usually mono- or tetra-hydrate), percarbonate, persulfate, perphosphate, persilicate salts, in combination with a peracid-forming bleach activator. The term bleach activator is meant herein as a compound which reacts with hydrogen peroxide to form a peracid via perhydrolysis. The peracid thus formed constitutes the activated bleach. Suitable bleach activators to be used herein include those belonging to the class of esters, amides, imides or anhydrides. Suitable examples are tetraacetylethylenediamine (TAED), sodium 4-[(3,5,5-trimethylhexanoyl)oxy]benzene-1-sulfonate (ISONOBS), 4-(dodecanoyloxy)benzene-1-sulfonate (LOBS), 4-(decanoyloxy)benzene-1-sulfonate, 4-(decanoyloxy)benzoate (DOBS or DOBA), 4-(nonanoyloxy)benzene-1-sulfonate (NOBS), and/or those disclosed in WO98/17767. A particular family of bleach activators of interest was disclosed in EP624154 and particulary preferred in that family is acetyl triethyl citrate (ATC). ATC or a short chain triglyceride like triacetin has the advantage that it is environmentally friendly Furthermore acetyl triethyl citrate and triacetin have good hydrolytical stability in the product upon storage and are efficient bleach activators. Finally, ATC is multifunctional, as the citrate released in the perhydrolysis reaction may function as a builder. Alternatively, the bleaching system may comprise peroxyacids of, for example, the amide, imide, or sulfone type. The bleaching system may also comprise peracids such as 6-(phthalimido)peroxyhexanoic acid (PAP). The bleaching system may also include a bleach catalyst. In some embodiments the bleach component may be an organic catalyst selected from the group consisting of organic catalysts having the following formulae:

(i) 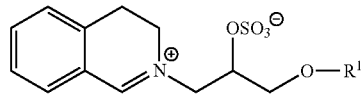

(ii) 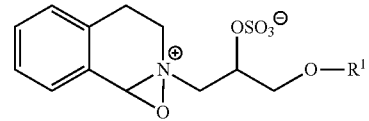

(iii) and mixtures thereof;
wherein each $R^1$ is independently a branched alkyl group containing from 9 to 24 carbons or linear alkyl group containing from 11 to 24 carbons, preferably each $R^1$ is independently a branched alkyl group containing from 9 to 18 carbons or linear alkyl group containing from 11 to 18 carbons, more preferably each $R^1$ is independently selected from the group consisting of 2-propylheptyl, 2-butyloctyl, 2-pentylnonyl, 2-hexyldecyl, dodecyl, tetradecyl, hexadecyl, octadecyl, isononyl, isodecyl, isotridecyl and isopentadecyl. Other exemplary bleaching systems are described, e.g. in WO2007/087258, WO2007/087244, WO2007/087259, EP1867708 (Vitamin K) and WO2007/087242. Suitable photobleaches may for example be sulfonated zinc or aluminium phthalocyanines.

Preferably the bleach component comprises a source of peracid in addition to bleach catalyst, particularly organic bleach catalyst. The source of peracid may be selected from (a) preformed peracid; (b) percarbonate, perborate or persulfate salt (hydrogen peroxide source) preferably in combination with a bleach activator; and (c) perhydrolase enzyme and an ester for forming peracid in situ in the presence of water in a textile or hard surface treatment step.

The detergent may comprise 0-10% by weight, such as 0.5-5%, 2-5%, 0.5-2% or 0.2-1% of a polymer. Any polymer known in the art for use in detergents may be utilized. The polymer may function as a co-builder as mentioned above, or may provide antiredeposition, fiber protection, soil release, dye transfer inhibition, grease cleaning and/or antifoaming properties. Some polymers may have more than one of the above-mentioned properties and/or more than one of the below-mentioned motifs. Exemplary polymers include (carboxymethyl)cellulose (CMC), poly(vinyl alcohol) (PVA), poly(vinylpyrrolidone) (PVP), poly(ethyleneglycol) or poly(ethylene oxide) (PEG), ethoxylated poly (ethyleneimine), carboxymethyl inulin (CMI), and polycarboxylates such as PAA, PAA/PMA, poly-aspartic acid, and lauryl methacrylate/acrylic acid copolymers, hydrophobically modified CMC (HM-CMC) and silicones, copolymers of terephthalic acid and oligomeric glycols, copolymers of poly(ethylene terephthalate) and poly (oxyethene terephthalate) (PET-POET), PVP, poly(vinylimidazole) (PVI), poly(vinylpyridine-N-oxide) (PVPO or PVPNO) and polyvinylpyrrolidone-vinylimidazole (PVPVI). Further exemplary polymers include sulfonated polycarboxylates, polyethylene oxide and polypropylene oxide (PEO-PPO) and diquaternium ethoxy sulfate. Other exemplary polymers are disclosed in, e.g., WO 2006/130575. Salts of the above-mentioned polymers are also contemplated.

The detergent compositions of the present invention may also comprise fabric hueing agents such as dyes or pigments, which when formulated in detergent compositions can deposit onto a fabric when said fabric is contacted with a wash liquor comprising said detergent compositions and thus altering the tint of said fabric through absorption/reflection of visible light. Fluorescent whitening agents emit at least some visible light. In contrast, fabric hueing agents alter the tint of a surface as they absorb at least a portion of the visible light spectrum. Suitable fabric hueing agents include dyes and dye-clay conjugates, and may also include pigments. Suitable dyes include small molecule dyes and polymeric dyes. Suitable small molecule dyes include small molecule dyes selected from the group consisting of dyes falling into the Colour Index (C.I.) classifications of Direct Blue, Direct Red, Direct Violet, Acid Blue, Acid Red, Acid Violet, Basic Blue, Basic Violet and Basic Red, or mixtures thereof, for example as described in WO2005/03274, WO2005/03275, WO2005/03276 and EP1876226 (hereby incorporated by reference). The detergent composition preferably comprises from about 0.00003 wt % to about 0.2 wt %, from about 0.00008 wt % to about 0.05 wt %, or even from about 0.0001 wt % to about 0.04 wt % fabric hueing agent. The composition may comprise from 0.0001 wt % to 0.2 wt % fabric hueing agent, this may be especially preferred when the composition is in the form of a unit dose pouch. Suitable hueing agents are also disclosed in, e.g. WO 2007/087257 and WO2007/087243.

It is at present contemplated that in the detergent compositions any enzyme, in particular the alpha amylase polypeptides of the invention, may be added in an amount corresponding to 0.01-100 mg of enzyme protein per liter of wash liquor, preferably 0.05-5 mg of enzyme protein per liter of wash liquor, in particular 0.1-1 mg of enzyme protein per liter of wash liquor.

The alpha amylase polypeptides of the invention may additionally be incorporated in the detergent formulations disclosed in WO 2006/002643, which is hereby incorporated as reference.

Uses

The present invention is also directed to methods for using a variant of the invention. The use may be in detergents, in particular laundry detergent compositions and dishwashing detergent compositions. Accordingly, the present invention relates to the use of a variant of a parent alpha-amylase, wherein the variant has alpha-amylase activity and has at least 89% sequence identity to SEQ ID NO: 1, wherein the variant comprises an amino acid motif of FX1X2K (SEQ ID NO: 4) at positions corresponding to amino acids 180 to 183 of SEQ ID NO: 2, wherein X1 is R or S; and X2 may be selected from A, R, N, D, C, E, Q, G, H, I, L, K, M, F, P, S, T, W, Y, and V with the proviso that when X1 is R, then X2 is not S, said variant has an improved Residual Activity (RA) compared to an amylase comprising the motif FRSK (SEQ ID NO: 7).

Thus, the invention provides the use of a variant of a parent or composition of the invention, in a domestic or industrial cleaning process. In particular, the invention relates to use of a variant according to the invention in laundry, dishwash; such as automatic or manual dishwash, hard surface cleaning, industrial and institutional cleaning, textile desizing, starch modification, starch liquefaction, saccharification, feed, baking, or brewing.

In one embodiment, the use is cleaning of fabric, for example laundry.

In another embodiment, the use is cleaning of ceramic, plastic or glass material, for example dishwashing.

Accordingly, the alpha-amylase polypeptides of the invention are applicable as a component in washing, dishwashing, and hard surface cleaning detergent compositions (in either a domestic or industrial setting).

The alpha-amylase variants of this invention possess valuable properties allowing for a variety of other industrial applications. For example, alpha-amylase polypeptides of the invention may be used for starch processes, in particular starch conversion, especially liquefaction of starch (see, e.g., U.S. Pat. No. 3,912,590, EP patent application nos. 252 730 and 63 909, WO 99/19467, and WO 96/28567 all references hereby incorporated by reference). Also contemplated are compositions for starch conversion purposes, which may beside the variant of the invention also comprise a glucoamylase, pullulanase, and other alpha-amylases.

Furthermore, alpha-amylase variants of this invention are also particularly useful in the production of sweeteners and ethanol (see, e.g., U.S. Pat. No. 5,231,017 hereby incorporated by reference), such as fuel, drinking and industrial ethanol, from starch or whole grains.

Alpha-amylase variants of the invention may also be useful for desizing of textiles, fabrics and garments (see, e.g., WO 95/21247, U.S. Pat. No. 4,643,736, EP 119,920 hereby in corporate by reference), beer making or brewing, in pulp and paper production.

Starch Conversion

Conventional starch-conversion processes, such as liquefaction and saccharification processes are described, e.g., in U.S. Pat. No. 3,912,590 and EP patent publications Nos. 252,730 and 63,909, hereby incorporated by reference.

In an embodiment the starch conversion process degrading starch to lower molecular weight carbohydrate components such as sugars or fat replacers includes a debranching step.

In the case of converting starch into a sugar, the starch is depolymerized. Such depolymerization processes may consist of a pre-treatment step and two or three consecutive process steps, viz. a liquefaction process, a saccharification process and dependent on the desired end product optionally an isomerization process.

(i) Pre-Treatment of Native Starch

Native starch consists of microscopic granules, which are insoluble in water at room temperature. When an aqueous starch slurry is heated, the granules swell and eventually burst, dispersing the starch molecules into the solution. During this "gelatinization" process there is a dramatic increase in viscosity. As the solids level is 30-40% in a typically industrial process, the starch has to be thinned or "liquefied" so that it can be handled. This reduction in viscosity is today mostly obtained by enzymatic degradation.

(ii) Liquefaction

During the liquefaction step, the long chained starch is degraded into branched and linear shorter units (maltodextrins) by an alpha-amylase. The liquefaction process is carried out at 105-110° C. for 5 to 10 minutes followed by 1-2 hours at 95° C. The pH lies between 5.5 and 6.2. In order to ensure optimal enzyme stability under these conditions, 1 mM of calcium is added (40 ppm free calcium ions). After this treatment the liquefied starch will have a "dextrose equivalent" (DE) of 10-15.

(iii) Saccharification

After the liquefaction process the maltodextrins are converted into dextrose by addition of a glucoamylase (e.g., AMG) and a debranching enzyme, such as an isoamylase (U.S. Pat. No. 4,335,208) or a pullulanase (e.g., Promozyme™) (U.S. Pat. No. 4,560,651). Before this step the pH is reduced to a value below 4.5, maintaining the high temperature (above 95° C.) to inactivate the liquefying alpha-amylase to reduce the formation of short oligosaccharide called "panose precursors" which cannot be hydrolyzed properly by the debranching enzyme.

The temperature is lowered to 60° C., and glucoamylase and debranching enzyme are added. The saccharification process proceeds for 24-72 hours.

Normally, when denaturing the α-amylase after the liquefaction step about 0.2-0.5% of the saccharification product is the branched trisaccharide 6<2>-alpha-glucosyl maltose (panose) which cannot be degraded by a pullulanase. If active amylase from the liquefaction step is present during saccharification (i.e., no denaturing), this level can be as high as 1-2%, which is highly undesirable as it lowers the saccharification yield significantly.

When using an amylase, saccharification optimally is conducted at a temperature range of about 30° C. to about 75° C., e.g., 45° C. to 75° C. or 47° C. to 74° C. The saccharifying may be conducted over a pH range of about pH 3 to about pH 7, e.g., pH 3.0 to pH 7.5, pH 3.5 to pH 5.5, pH3.5, pH 3.8, or pH 4.5.

(iv) Isomerization

When the desired final sugar product is, e.g., high fructose syrup the dextrose syrup may be converted into fructose. After the saccharification process the pH is increased to a value in the range of 6-8, preferably pH 7.5, and the calcium is removed by ion exchange. The dextrose syrup is then converted into high fructose syrup using, e.g., an immmobilized glucoseisomerase (such as Sweetzyme™ IT).

Ethanol Production

In general alcohol production (ethanol) from whole grain can be separated into 4 main steps
Milling
Liquefaction
Saccharification
Fermentation (i) Milling The grain is milled in order to open up the structure and allowing for further processing. Two processes are used wet or dry milling. In dry milling the whole kernel is milled and used in the remaining part of the process. Wet milling gives a very good separation of germ and meal (starch granules and protein) and is with a few exceptions applied at locations where there is a parallel production of syrups.

(ii) Liquefaction

In the liquefaction process the starch granules are solubilized by hydrolysis to maltodextrins mostly of a DP higher than 4. The hydrolysis may be carried out by acid treatment or enzymatically by alpha-amylase. Acid hydrolysis is used on a limited basis. The raw material can be milled whole grain or a side stream from starch processing.

Enzymatic liquefaction is typically carried out as a three-step hot slurry process. The slurry is heated to between 60-95° C., preferably 80-85° C., and the enzyme(s) is (are) added. Then the slurry is jet-cooked at between 95-140° C., preferably 105-125° C., cooled to 60-95° C. and more enzyme(s) is (are) added to obtain the final hydrolysis. The liquefaction process is carried out at pH 4.5-6.5, typically at a pH between 5 and 6. Milled and liquefied grain is also known as mash.

(iii) Saccharification

To produce low molecular sugars DP1-3 that can be metabolized by yeast, the maltodextrin from the liquefaction must be further hydrolyzed. The hydrolysis is typically done enzymatically by glucoamylases, alternatively alpha-glucosidases or acid alpha-amylases can be used. A full saccharification step may last up to 72 hours, however, it is common only to do a pre-saccharification of typically 4 hours and then complete saccharification during fermentation (SSF). Saccharification is typically carried out at temperatures from 30-65° C., typically around 60° C., and at pH 4.5.

(iv) Fermentation

Yeast typically from *Saccharomyces* spp. is added to the mash and the fermentation is ongoing for 24-96 hours, such as typically 35-60 hours. The temperature is between 26-34° C., typically at about 32° C., and the pH is from pH 3-6, preferably around pH 4-5.

Note that the most widely used process is a simultaneous saccharification and fermentation (SSF) process where there is no holding stage for the saccharification, meaning that yeast and enzyme is added together. When doing SSF it is common to introduce a pre-saccharification step at a temperature above 50° C., just prior to the fermentation.

(v) Distillation

Following the fermentation the mash is distilled to extract the ethanol.

The ethanol obtained according to the process of the invention may be used as, e.g., fuel ethanol; drinking ethanol, i.e., potable neutral spirits; or industrial ethanol.

(vi) By-Products

Left over from the fermentation is the grain, which is typically used for animal feed either in liquid form or dried.

Further details on how to carry out liquefaction, saccharification, fermentation, distillation, and recovering of ethanol are well known to the skilled person.

According to the process of the invention the saccharification and fermentation may be carried out simultaneously or separately.

Pulp and Paper Production

Alkaline alpha-amylase polypeptides of the invention may also be used in the production of lignocellulosic materials, such as pulp, paper and cardboard, from starch reinforced waste paper and cardboard, especially where re-pulping occurs at pH above 7 and where amylases facilitate the disintegration of the waste material through degradation of the reinforcing starch. The alpha-amylase of the invention is especially useful in a process for producing a papermaking pulp from starch-coated printed-paper. The process may be performed as described in WO 95/14807, comprising the following steps:

a) disintegrating the paper to produce a pulp,
b) treating with a starch-degrading enzyme before, during or after step a), and
c) separating ink particles from the pulp after steps a) and b).

The alpha-amylases of the invention may also be very useful in modifying starch where enzymatically modified starch is used in papermaking together with alkaline fillers such as calcium carbonate, kaolin and clays. With the alkaline alpha-amylases of the invention it becomes possible to modify the starch in the presence of the filler thus allowing for a simpler integrated process.

Desizing of Textiles, Fabrics and Garments

An alpha-amylase of the invention may also be very useful in textile, fabric or garment desizing. In the textile processing industry, alpha-amylases are traditionally used as auxiliaries in the desizing process to facilitate the removal of starch-containing size, which has served as a protective coating on weft yarns during weaving. Complete removal of the size coating after weaving is important to ensure optimum results in the subsequent processes, in which the fabric is scoured, bleached and dyed. Enzymatic starch breakdown is preferred because it does not involve any harmful effect on the fiber material. In order to reduce processing cost and increase mill throughput, the desizing processing is sometimes combined with the scouring and bleaching steps. In such cases, non-enzymatic auxiliaries such as alkali or oxidation agents are typically used to break down the starch, because traditional alpha-amylases are not very compatible with high pH levels and bleaching agents. The non-enzymatic breakdown of the starch size does lead to some fiber damage because of the rather aggressive chemicals used. Accordingly, it would be desirable to use the alpha-amylases of the invention as they have an improved performance in alkaline solutions. The alpha-amylases may be used alone or in combination with a cellulase when desizing cellulose-containing fabric or textile.

Desizing and bleaching processes are well known in the art. For instance, such processes are described in WO 95/21247, U.S. Pat. No. 4,643,736, EP 119,920 hereby incorporate by reference.

Commercially available products for desizing include AQUAZYME® and AQUAZYME® ULTRA from Novozymes A/S.

Beer Making

The alpha-amylases of the invention may also be very useful in a beer-making process; the alpha-amylases will typically be added during the mashing process.

The present invention is further described by the following examples that should not be construed as limiting the scope of the invention.

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

EXAMPLES

Example 1: Assays for Alpha-Amylase Activity

1. Phadebas Assay

Alpha-amylase activity may be determined by a method employing Phadebas® tablets as substrate. Phadebas tablets (Phadebas® Amylase Test, supplied by Pharmacia Diagnostic) contain a cross-linked insoluble blue-colored starch polymer, which has been mixed with bovine serum albumin and a buffer substance and tableted.

For every single measurement one tablet is suspended in a tube containing 5 ml 100 mM Britton-Robinson buffer (100 mM acetic acid, 100 mM phosphoric acid, 100 mM boric acid, 0.1 mM $CaCl_2$), pH adjusted to the value of interest with NaOH). The test is performed in a water bath at the temperature of interest. The alpha-amylase to be tested is diluted in x ml of 100 mM Britton-Robinson buffer. 1 ml of this alpha-amylase solution is added to the 5 ml 100 mM Britton-Robinson buffer. The starch is hydrolyzed by the alpha-amylase giving soluble blue fragments. The absorbance of the resulting blue solution, measured spectrophotometrically at 620 nm, is a function of the alpha-amylase activity.

It is important that the measured 620 nm absorbance after 10 or 15 minutes of incubation (testing time) is in the range of 0.2 to 2.0 absorbance units at 620 nm. In this absorbance range there is linearity between activity and absorbance (Lambert-Beer law). The dilution of the enzyme must therefore be adjusted to fit this criterion. Under a specified set of conditions (temp., pH, reaction time, buffer conditions) 1 mg of a given alpha-amylase will hydrolyze a certain amount of substrate and a blue colour will be produced. The colour intensity is measured at 620 nm. The measured absorbance is directly proportional to the specific activity (activity/mg of pure alpha-amylase protein) of the alpha-amylase in question under the given set of conditions.

2. PNP-G7 Assay

Alpha-amylase activity is determined by a method employing the PNP-G7 substrate. PNP-G7 which is an abbreviation for p-nitrophenyl-alpha,D-maltoheptaoside is a blocked oligosaccharide which can be cleaved by an endo-amylase. Following the cleavage, the alpha-Glucosidase included in the kit digest the substrate to liberate a free PNP molecule which has a yellow colour and thus can be measured by visible spectophometry at $\lambda$=405 nm (400-420 nm). Kits containing PNP-G7 substrate and alpha-Glucosidase is manufactured by Boehringer-Mannheim (cat. No. 1054635).

To prepare the reagent solution 10 ml of substrate/buffer solution is added to 50 ml enzyme/buffer solution as recommended by the manufacturer. The assay is performed by transferring 20 microlsample to a 96 well microtitre plate and incubating at 25° C. 200 microlreagent solution pre-equilibrated to 25° C. is added. The solution is mixed and pre-incubated 1 minute and absorption is measured every 30 sec. over 4 minutes at OD 405 nm in an ELISA reader.

The slope of the time dependent absorption-curve is directly proportional to the activity of the alpha-amylase in question under the given set of conditions.

Example 2: Residual Activity of Alpha-Amylase Variants of the Invention

Two amino acid deletions were introduced in alpha-amylase TS23-truncated (SEQ ID NO: 1) by standard site directed methods. In the resulting alpha-amylase variant, different combinations of two amino acid deletions in the R180-S181-T182-G183 region were introduced as indicated in Table 1 below. The position numbering is according to SEQ ID NO: 1 The modified amylase genes were transformed into and expressed in *Bacillus subtilis*. The *Bacillus subtilis* broths were centrifuged and the amylase containing supernatants isolated and diluted at least 50 times in Britton-Robinson buffer pH 7.3 before they were mixed with in 90% Model A detergent with 0.3% EDTA. The samples were then split in two samples; one was stored at 4° C. and the other was incubated at 40° C. for 4 hours. Following that, the samples were diluted 10 times in 100 mM Britton-Robinson buffer (100 mM acetic acid+100 mM phosphate acid+100 mM boric acid, pH 7.3+0.12 mM $CaCl_2$)+0.01% Brij, pH adjusted to pH 7.3) and the amylase activity measured using Phadebas amylase assay as described under methods. The residual activities were calculated as the ratio between the activity in the samples that have been incubated at 40° C. relative to activity in the samples that have been incubated at 4° C.

TABLE 1

Residual activity (RA) of alpha-amylase variants after incubation in detergent with EDTA

| Variant no. | Amylase variants | Resulting motif | RA | Improvement factor (IF) | Half life |
|---|---|---|---|---|---|
| A | SEQ ID NO: 1 + R180* + S181* | FTGK (SEQ ID NO: 6) | 11 | 1 | 1.26 |

TABLE 1-continued

Residual activity (RA) of alpha-amylase variants after incubation in detergent with EDTA

| Variant no. | Amylase variants | Resulting motif | RA | Improvement factor (IF) | Half life |
|---|---|---|---|---|---|
| B | SEQ ID NO: 1 + T182* + G183* | FRSK (SEQ ID NO: 7) | 22 | 2 | 1.83 |
| C | SEQ ID NO: 1 + S181* + T182* | FRGK (SEQ ID NO: 8) | 22 | 2 | 1.83 |
| D | SEQ ID NO: 1 + R180* + T182* | FSGK (SEQ ID NO: 9) | 32 | 2.9 | 2.43 |
| E | SEQ ID NO: 1 + R180* + G183* | FSTK (SEQ ID NO: 10) | 36 | 3.3 | 2.71 |
| F | SEQ ID NO: 1 + R180* + T182G + G183* | FSGK (SEQ ID NO: 9) | 37 | 2.5 | 2.77 |
| G | SEQ ID NO: 1 + R180* + T182T + G183* | FSTK (SEQ ID NO: 10) | 34 | 2.3 | 2.55 |
| H | SEQ ID NO: 1 + S181* + T182C + G183* | FRCK (SEQ ID NO: 11) | 37 | 2.6 | 2.79 |
| I | SEQ ID NO: 1 + S181* + T182Y + G183* | FRYK (SEQ ID NO: 12) | 32 | 2.2 | 2.42 |
| J | SEQ ID NO: 1 + R180 + T182I + G183* | FSIK (SEQ ID NO: 13) | 31 | 2.1 | 2.34 |
| K | SEQ ID NO: 1 + R180* + T182L + G183* | FSLK (SEQ ID NO: 14) | 54 | 3.7 | 4.45 |
| L | SEQ ID NO: 1 + S181* + T182L + G183* | FRLK (SEQ ID NO: 15) | 47 | 3.3 | 3.71 |
| M | SEQ ID NO: 1 + R180* + T182Q + G183* | FSQK (SEQ ID NO: 16) | 34 | 2.3 | 2.58 |
| N | SEQ ID NO: 1 + R180* + T182S + G183* | FSSK (SEQ ID NO: 17) | 61 | 4.2 | 5.54 |

This example demonstrates that alpha-amylase variant having increased stability in the presence of detergent with EDTA can be generated by deleting two amino acids, and the largest effect is clearly observed by preserving a Serine, Threonine and/or a Glycine in amino acid motif.

Example 3: Comparative Data on Residual Activity (RA)

Similar to Example 2, two amino acid deletions were introduced in the alpha-amylase SP722 (SEQ ID NO: 5) by standard site directed methods. In the resulting alpha-amylase variant, different combinations of two amino acid deletions in the R181-G182-D183-G184 region were introduced as indicated in Table 2 below. The position numbering is according to SEQ ID NO: 5. The modified amylase genes were transformed into and expressed in Bacillus subtilis. The Bacillus subtilis broths were centrifuged and the amylase containing supernatants isolated and diluted at least 50 times in Britton-Robinson buffer pH 7.3 before they were mixed with in 90% Model A detergent with 0.3% EDTA. The samples were then split in two samples; one was stored at 4° C. and the other was incubated at 45° C. for 4 hours. Following that, the samples were diluted 10 times in 100 mM Britton-Robinson buffer (100 mM acetic acid+100 mM phosphate acid+100 mM boric acid, pH 7.3+0.12 mM $CaCl_2$)+0.01% Brij, pH adjusted to pH 7.3) and the amylase activity measured using Phadebas amylase assay as described under methods. The residual activities were calculated as the ratio between the activity in the samples that have been incubated at 45° C. relative to activity in the samples that have been incubated at 4° C.

TABLE 2

Residual Activity (RA) of alpha-amylase variants known in the art after incubation in detergent with EDTA

| Variant no. | Corresponding variant in Table 1 | Amylase variants | Resulting motif | RA % | Improvement factor (IF) |
|---|---|---|---|---|---|
| 1 | C | SP722 + G182* + D183* | FRGK (SEQ ID NO: 8) | 88 | 1 |
| 2 | D | SP722 + R181* + G182* + D183S | FSGK (SEQ ID NO: 9) | 96 | 1.1 |
| 3 | E | SP722 + R181* + G182* + D183S + G184T | FSTK (SEQ ID NO: 10) | 59 | 0.7 |
| 4 | — | SP722 + R181* + G182* + D183S + G184S | FSSK (SEQ ID NO: 17) | 80 | 0.9 |

Example 4: Comparative Data on Residual Activity (RA)

Similar to Examples 2 and 3, two amino acid deletions were introduced in the alpha-amylase SP722 (SEQ ID NO: 5) by standard site directed methods. The Residual Activity (RA) was determined after a slightly longer incubation compared to the two previous Examples (Present variants were incubated for 18 hours instead of 4 hours). In the resulting alpha-amylase variant, different combinations of two amino acid deletions in the R181-G182-D183-G184 region were introduced as indicated in Table 3 below. The position numbering is according to SEQ ID NO: 5. The modified amylase genes were transformed into and expressed in Bacillus subtilis. The Bacillus subtilis broths were centrifuged and the amylase containing supernatants isolated and diluted at least 50 times in Britton-Robinson buffer pH 7.3 before they were mixed with in 90% Model A detergent with 0.3% EDTA. The samples were then split in two samples; one was stored at 4° C. and the other was incubated at 45° C. for 18 hours. Following that, the samples were diluted 10 times in 100 mM Britton-Robinson buffer (100 mM acetic acid+100 mM phosphate acid+100 mM boric acid, pH 7.3+0.12 mM $CaCl_2$)+0.01% Brij, pH adjusted to pH 7.3) and the amylase activity measured using Phadebas amylase assay as described under methods. The residual activities were calculated as the ratio between the activity in the samples that have been incubated at 45° C. relative to activity in the samples that have been incubated at 4° C.

TABLE 3

Residual Activity (RA) of alpha-amylase variants known in the art after incubation in detergent with EDTA

| Variant no. | Amylase variants | Resulting motif | RA % | Improvement factor (IF) | Half life (hrs) |
|---|---|---|---|---|---|
| 1 | SP722 + G182* + D183* | FRGK (SEQ ID NO: 8) | 31 | 1 | 11 |
| 5 | SP722 + G182* + D183D + G184* | FRDK (SEQ ID NO: 18) | 20 | 0.7 | 7.8 |
| 6 | SP722 + G182* + D183A + G184* | FRAK (SEQ ID NO: 19) | 0 | 0 | 2.1 |
| 7 | SP722 + G182* + D183R + G184* | FRRK (SEQ ID NO: 20) | 2 | 0.1 | 3.1 |
| 8 | SP722 + G182* + D183N + G184* | FRNK (SEQ ID NO: 21) | 3 | 0.1 | 3.7 |
| 9 | SP722 + G182* + D183E + G184* | FREK (SEQ ID NO: 22) | 2 | 0.1 | 3.2 |
| 10 | SP722 + G182* + D183Q + G184* | FRQK (SEQ ID NO: 23) | 4 | 0.1 | 3.9 |
| 11 | SP722 + G182* + D183H + G184* | FRHK (SEQ ID NO: 24) | 3 | 0.1 | 3.4 |
| 12 | SP722 + G182* + D183I + G184* | FRIK (SEQ ID NO: 25) | 6 | 0.2 | 4.5 |
| 13 | SP722 + G182* + D183L + G184* | FRLK (SEQ ID NO: 15) | 17 | 0.5 | 6.9 |
| 14 | SP722 + G182* + D183K + G184* | FRKK (SEQ ID NO: 26) | 2 | 0.1 | 3.3 |
| 15 | SP722 + G182* + D183M + G184* | FRMK (SEQ ID NO: 27) | 0 | 0 | 2.2 |
| 16 | SP722 + G182* + D183F + G184* | FRFK (SEQ ID NO: 28) | 0 | 0 | 0 |
| 17 | SP722 + G182* + D183T + G184* | FRTK (SEQ ID NO: 29) | 14 | 0.4 | 6.3 |
| 18 | SP722 + G182* + D183W + G184* | FRWK (SEQ ID NO: 30) | 0 | 0 | 0 |
| 19 | SP722 + G182* + D183Y + G184* | FRYK (SEQ ID NO: 12) | 1 | 0 | 2.8 |
| 20 | SP722 + G182* + D183V + G184* | FRVK (SEQ ID NO: 31) | 0 | 0 | 0 |
| 21 | SP722 + R181* + G182S + D183A + G184* | FSAK (SEQ ID NO: 32) | 14 | 0.5 | 6.3 |
| 22 | SP722 + R181* + G182S + D183R + G184* | FSRK (SEQ ID NO: 33) | 3 | 0.1 | 3.6 |
| 23 | SP722 + R181* + G182S + D183N + G184* | FSNK (SEQ ID NO: 34) | 24 | 0.8 | 8.7 |
| 24 | SP722 + R181* + G182S + D183E + G184* | FSEK (SEQ ID NO: 35) | 8 | 0.2 | 4.8 |
| 25 | SP722 + R181* + G182S + D183L + G184* | FSLK (SEQ ID NO: 14) | 23 | 0.7 | 8.4 |
| 26 | SP722 + R181* + G182S + D183K + G184* | FSKK (SEQ ID NO: 36) | 13 | 0.4 | 6.2 |
| 27 | SP722 + R181* + G182S + D183F + G184* | FSFK (SEQ ID NO: 37) | 10 | 0.3 | 5.4 |
| 28 | SP722 + R181* + G182S + D183P + G184* | FSPK (SEQ ID NO: 38) | 4 | 0.1 | 3.8 |
| 29 | SP722 + R181* + G182S + D183W + G184* | FSWK (SEQ ID NO: 39) | 2 | 0.1 | 3.2 |
| 30 | SP722 + R181* + G182S + D183Y + G184* | FSYK (SEQ ID NO: 40) | 16 | 0.5 | 6.7 |
| 31 | SP722 + R181* + G182S + D183V + G184* | FSVK (SEQ ID NO: 41) | 8 | 0.3 | 4.9 |
| 32 | SP722 + R181* + G182S + D183D + G184* | FSDK (SEQ ID NO: 42) | 0 | 0 | 0 |
| 33 | SP722 + R181* + G182S + D183M + G184* | FSMK (SEQ ID NO: 43) | 2 | 0.1 | 3.3 |
| 34 | SP722 + R181* + G182S + D183P + G184* | FSPK (SEQ ID NO: 38) | 8 | 0.2 | 4.8 |
| 35 | SP722 + R181* + G182S + D183T + G184* | FSTK (SEQ ID NO: 10) | 10 | 0.3 | 5.5 |

The invention claimed is:

1. An alpha-amylase variant, wherein said variant has alpha-amylase activity and comprises an amino acid sequence that has at least 89% sequence identity to the amino acid sequence of SEQ ID NO: 1, wherein said variant comprises an amino acid motif selected from the group consisting of FRCK (SEQ ID NO: 11), FRYK (SEQ ID NO: 12), FSIK (SEQ ID NO: 13), FSLK (SEQ ID NO: 14), FRLK (SEQ ID NO: 15), FSQK (SEQ ID NO: 16) and FSSK (SEQ ID NO: 17) at the positions corresponding to amino acids 179 to 182 of SEQ ID NO: 2; and wherein said variant has improved stability in a detergent compared to an alpha-amylase comprising the amino acid sequence of SEQ ID NO: 2 with the amino acid motif FTGK (SEQ ID NO: 6) at the positions corresponding to amino acids 179 to 182 of SEQ ID NO: 2, wherein stability is determined by a PHADEBAS amylase assay.

2. The variant according to claim 1, wherein at least one of the positions corresponding to Y242 and F266 of SEQ ID NO: 2 is substituted with another amino acid.

3. The variant according to claim 2, wherein said substitution in position Y242 is Y242F and said substitution in position F266 is F266Y.

4. The variant according to claim 1, wherein said variant has at least 90%, at least 91%, at least 92%, at least 93%, at least 94%, at least 95%, at least 96%, at least 97%, at least 98%, or at least 99% sequence identity to the amino acid sequence of SEQ ID NO: 1 or 3.

5. A composition comprising the variant according to claim 1.

6. The composition according to claim 5, which is a cleaning composition.

7. The composition according to claim 5, wherein said composition further comprises a detergent component selected from the group consisting of a surfactant, builder, bleaching systems, bleach activator, polymers, fabric hueing agents, and combinations thereof.

8. The composition according to claim 5, wherein said composition is formulated as a liquid, solid, soap bar, film, unit doses, or pouch detergent composition.

9. The composition according to claim 5, which further comprises at least one additional enzyme selected from the group consisting of a protease, a lipase, a peroxidase, a glucanase, another amylolytic enzyme, a cellulase, and combinations thereof.

10. A detergent additive comprising the variant according to claim 1, optionally in the form of a non-dusting granulate, stabilized liquid, or protected enzyme.

11. The detergent additive according to claim 10, comprising 0.02-200 mg of enzyme protein per gram of said additive.

12. The detergent additive according to claim 10, which comprises at least one additional enzyme selected from the group consisting of a protease, a lipase, a peroxidase, a glucanase, another amylolytic enzyme, a cellulase, and combinations thereof.

13. A manual or automatic dishwashing detergent composition comprising the variant according to claim 1, and optionally a surfactant.

14. The manual or automatic dishwashing detergent composition according to claim 13, which comprises at least one additional enzyme selected from the group consisting of a protease, a lipase, a peroxidase, a glucanase, another amylolytic enzyme, a cellulase, and combinations thereof.

15. A manual or automatic laundry detergent composition comprising the variant according to claim 1.

16. The manual or automatic laundry detergent composition according to claim 15, which comprises at least one additional enzyme selected from the group consisting of a protease, a lipase, a peroxidase, a glucanase, another amylolytic enzyme, a cellulase, and combinations thereof.

17. A polynucleotide comprising a nucleotide sequence encoding the variant according to claim 1.

18. A nucleic acid construct comprising said polynucleotide according to claim 17.

19. An expression vector comprising said polynucleotide according to claim 17.

20. An isolated host cell comprising said polynucleotide according to claim 17.

21. A method of producing the alpha-amylase variant of claim 1, comprising:
   a. providing an isolated host cell comprising a polynucleotide, wherein the polynucleotide comprises a nucleotide sequence encoding the variant according to claim 1;
   b. cultivating the isolated host cell under conditions suitable for expression of said variant; and
   c. recovering said variant.

* * * * *

SEQUENCE LISTING

<160> NUMBER OF SEQ ID NOS: 43

<210> SEQ ID NO 1
<211> LENGTH: 484
<212> TYPE: PRT
<213> ORGANISM: Bacillus species

<400> SEQUENCE: 1

Asn Thr Ala Pro Ile Asn Glu Thr Met Met Gln Tyr Phe Glu Trp Asp
1               5                   10                  15

Leu Pro Asn Asp Gly Thr Leu Trp Thr Lys Val Lys Asn Glu Ala Ala
            20                  25                  30

Asn Leu Ser Ser Leu Gly Ile Thr Ala Leu Trp Leu Pro Pro Ala Tyr
        35                  40                  45

```
Lys Gly Thr Ser Gln Ser Asp Val Gly Tyr Gly Val Tyr Asp Leu Tyr
 50                  55                  60

Asp Leu Gly Glu Phe Asn Gln Lys Gly Thr Ile Arg Thr Lys Tyr Gly
 65                  70                  75                  80

Thr Lys Thr Gln Tyr Ile Gln Ala Ile Gln Ala Ala Lys Ala Ala Gly
                     85                  90                  95

Met Gln Val Tyr Ala Asp Val Val Phe Asn His Lys Ala Gly Ala Asp
                100                 105                 110

Gly Thr Glu Phe Val Asp Ala Val Glu Val Asp Pro Ser Asn Arg Asn
                115                 120                 125

Gln Glu Thr Ser Gly Thr Tyr Gln Ile Gln Ala Trp Thr Lys Phe Asp
    130                 135                 140

Phe Pro Gly Arg Gly Asn Thr Tyr Ser Ser Phe Lys Trp Arg Trp Tyr
145                 150                 155                 160

His Phe Asp Gly Thr Asp Trp Asp Glu Ser Arg Lys Leu Asn Arg Ile
                165                 170                 175

Tyr Lys Phe Arg Ser Thr Gly Lys Ala Trp Asp Trp Glu Val Asp Thr
                180                 185                 190

Glu Asn Gly Asn Tyr Asp Tyr Leu Met Phe Ala Asp Leu Asp Met Asp
                195                 200                 205

His Pro Glu Val Val Thr Glu Leu Lys Asn Trp Gly Thr Trp Tyr Val
210                 215                 220

Asn Thr Thr Asn Ile Asp Gly Phe Arg Leu Asp Ala Val Lys His Ile
225                 230                 235                 240

Lys Tyr Thr Phe Phe Pro Asp Trp Leu Thr Tyr Val Arg Asn Gln Thr
                245                 250                 255

Gly Lys Asn Leu Phe Ala Val Gly Glu Phe Trp Ser Tyr Asp Val Asn
                260                 265                 270

Lys Leu His Asn Tyr Ile Thr Lys Thr Asn Gly Ser Met Ser Leu Phe
                275                 280                 285

Asp Ala Pro Leu His Asn Asn Phe Tyr Thr Ala Ser Lys Ser Ser Gly
    290                 295                 300

Tyr Phe Asp Met Arg Tyr Leu Leu Asn Asn Thr Leu Met Lys Asp Gln
305                 310                 315                 320

Pro Ser Leu Ala Val Thr Leu Val Asp Asn His Asp Thr Gln Pro Gly
                325                 330                 335

Gln Ser Leu Gln Ser Trp Val Glu Pro Trp Phe Lys Pro Leu Ala Tyr
                340                 345                 350

Ala Phe Ile Leu Thr Arg Gln Glu Gly Tyr Pro Cys Val Phe Tyr Gly
                355                 360                 365

Asp Tyr Tyr Gly Ile Pro Lys Tyr Asn Ile Pro Gly Leu Lys Ser Lys
    370                 375                 380

Ile Asp Pro Leu Leu Ile Ala Arg Arg Asp Tyr Ala Tyr Gly Thr Gln
385                 390                 395                 400

Arg Asp Tyr Ile Asp His Gln Asp Ile Ile Gly Trp Thr Arg Glu Gly
                405                 410                 415

Ile Asp Thr Lys Pro Asn Ser Gly Leu Ala Ala Leu Ile Thr Asp Gly
                420                 425                 430

Pro Gly Gly Ser Lys Trp Met Tyr Val Gly Lys Lys His Ala Gly Lys
                435                 440                 445

Val Phe Tyr Asp Leu Thr Gly Asn Arg Ser Asp Thr Val Thr Ile Asn
    450                 455                 460
```

-continued

```
Ala Asp Gly Trp Gly Glu Phe Lys Val Asn Gly Gly Ser Val Ser Ile
465                 470                 475                 480

Trp Val Ala Lys

<210> SEQ ID NO 2
<211> LENGTH: 482
<212> TYPE: PRT
<213> ORGANISM: Bacillus species
<220> FEATURE:
<221> NAME/KEY: MISC_FEATURE
<222> LOCATION: (180)..(180)
<223> OTHER INFORMATION: Wherein X is R or S
<220> FEATURE:
<221> NAME/KEY: MISC_FEATURE
<222> LOCATION: (181)..(181)
<223> OTHER INFORMATION: Wherein X is A, R, N, D, C, E, Q, G, H, I, L,
      K, M, F, P, S, R, W, Y, or V

<400> SEQUENCE: 2

Asn Thr Ala Pro Ile Asn Glu Thr Met Met Gln Tyr Phe Glu Trp Asp
1               5                   10                  15

Leu Pro Asn Asp Gly Thr Leu Trp Thr Lys Val Lys Asn Glu Ala Ala
            20                  25                  30

Asn Leu Ser Ser Leu Gly Ile Thr Ala Leu Trp Leu Pro Pro Ala Tyr
        35                  40                  45

Lys Gly Thr Ser Gln Ser Asp Val Gly Tyr Gly Val Tyr Asp Leu Tyr
50                  55                  60

Asp Leu Gly Glu Phe Asn Gln Lys Gly Thr Ile Arg Thr Lys Tyr Gly
65                  70                  75                  80

Thr Lys Thr Gln Tyr Ile Gln Ala Ile Gln Ala Ala Lys Ala Ala Gly
                85                  90                  95

Met Gln Val Tyr Ala Asp Val Val Phe Asn His Lys Ala Gly Ala Asp
            100                 105                 110

Gly Thr Glu Phe Val Asp Ala Val Glu Val Asp Pro Ser Asn Arg Asn
        115                 120                 125

Gln Glu Thr Ser Gly Thr Tyr Gln Ile Gln Ala Trp Thr Lys Phe Asp
130                 135                 140

Phe Pro Gly Arg Gly Asn Thr Tyr Ser Ser Phe Lys Trp Arg Trp Tyr
145                 150                 155                 160

His Phe Asp Gly Thr Asp Trp Asp Glu Ser Arg Lys Leu Asn Arg Ile
                165                 170                 175

Tyr Lys Phe Xaa Xaa Lys Ala Trp Asp Trp Glu Val Asp Thr Glu Asn
            180                 185                 190

Gly Asn Tyr Asp Tyr Leu Met Phe Ala Asp Leu Asp Met Asp His Pro
        195                 200                 205

Glu Val Val Thr Glu Leu Lys Asn Trp Gly Thr Trp Tyr Val Asn Thr
210                 215                 220

Thr Asn Ile Asp Gly Phe Arg Leu Asp Ala Val Lys His Ile Lys Tyr
225                 230                 235                 240

Thr Phe Phe Pro Asp Trp Leu Thr Tyr Val Arg Asn Gln Thr Gly Lys
                245                 250                 255

Asn Leu Phe Ala Val Gly Glu Phe Trp Ser Tyr Asp Val Asn Lys Leu
            260                 265                 270

His Asn Tyr Ile Thr Lys Thr Asn Gly Ser Met Ser Leu Phe Asp Ala
        275                 280                 285

Pro Leu His Asn Asn Phe Tyr Thr Ala Ser Lys Ser Ser Gly Tyr Phe
        290                 295                 300
```

```
Asp Met Arg Tyr Leu Leu Asn Asn Thr Leu Met Lys Asp Gln Pro Ser
305                 310                 315                 320

Leu Ala Val Thr Leu Val Asp Asn His Asp Thr Gln Pro Gly Gln Ser
            325                 330                 335

Leu Gln Ser Trp Val Glu Pro Trp Phe Lys Pro Leu Ala Tyr Ala Phe
        340                 345                 350

Ile Leu Thr Arg Gln Glu Gly Tyr Pro Cys Val Phe Tyr Gly Asp Tyr
            355                 360                 365

Tyr Gly Ile Pro Lys Tyr Asn Ile Pro Gly Leu Lys Ser Lys Ile Asp
    370                 375                 380

Pro Leu Leu Ile Ala Arg Arg Asp Tyr Ala Tyr Gly Thr Gln Arg Asp
385                 390                 395                 400

Tyr Ile Asp His Gln Asp Ile Ile Gly Trp Thr Arg Glu Gly Ile Asp
                405                 410                 415

Thr Lys Pro Asn Ser Gly Leu Ala Ala Leu Ile Thr Asp Gly Pro Gly
                420                 425                 430

Gly Ser Lys Trp Met Tyr Val Gly Lys Lys His Ala Gly Lys Val Phe
            435                 440                 445

Tyr Asp Leu Thr Gly Asn Arg Ser Asp Thr Val Thr Ile Asn Ala Asp
    450                 455                 460

Gly Trp Gly Glu Phe Lys Val Asn Gly Gly Ser Val Ser Ile Trp Val
465                 470                 475                 480

Ala Lys

<210> SEQ ID NO 3
<211> LENGTH: 583
<212> TYPE: PRT
<213> ORGANISM: Bacillus species

<400> SEQUENCE: 3

Asn Thr Ala Pro Ile Asn Glu Thr Met Met Gln Tyr Phe Glu Trp Asp
1               5                   10                  15

Leu Pro Asn Asp Gly Thr Leu Trp Thr Lys Val Lys Asn Glu Ala Ala
            20                  25                  30

Asn Leu Ser Ser Leu Gly Ile Thr Ala Leu Trp Leu Pro Pro Ala Tyr
        35                  40                  45

Lys Gly Thr Ser Gln Ser Asp Val Gly Tyr Gly Val Tyr Asp Leu Tyr
    50                  55                  60

Asp Leu Gly Glu Phe Asn Gln Lys Gly Thr Ile Arg Thr Lys Tyr Gly
65                  70                  75                  80

Thr Lys Thr Gln Tyr Ile Gln Ala Ile Gln Ala Ala Lys Ala Ala Gly
                85                  90                  95

Met Gln Val Tyr Ala Asp Val Val Phe Asn His Lys Ala Gly Ala Asp
            100                 105                 110

Gly Thr Glu Phe Val Asp Ala Val Glu Val Asp Pro Ser Asn Arg Asn
        115                 120                 125

Gln Glu Thr Ser Gly Thr Tyr Gln Ile Gln Ala Trp Thr Lys Phe Asp
    130                 135                 140

Phe Pro Gly Arg Gly Asn Thr Tyr Ser Ser Phe Lys Trp Arg Trp Tyr
145                 150                 155                 160

His Phe Asp Gly Thr Asp Trp Asp Glu Ser Arg Lys Leu Asn Arg Ile
                165                 170                 175

Tyr Lys Phe Arg Ser Thr Gly Lys Ala Trp Asp Trp Glu Val Asp Thr
            180                 185                 190
```

```
Glu Asn Gly Asn Tyr Asp Tyr Leu Met Phe Ala Asp Leu Asp Met Asp
            195                 200                 205

His Pro Glu Val Val Thr Glu Leu Lys Asn Trp Gly Thr Trp Tyr Val
210                 215                 220

Asn Thr Thr Asn Ile Asp Gly Phe Arg Leu Asp Ala Val Lys His Ile
225                 230                 235                 240

Lys Tyr Ser Phe Phe Pro Asp Trp Leu Thr Tyr Val Arg Asn Gln Thr
                245                 250                 255

Gly Lys Asn Leu Phe Ala Val Gly Glu Phe Trp Ser Tyr Asp Val Asn
            260                 265                 270

Lys Leu His Asn Tyr Ile Thr Lys Thr Asn Gly Ser Met Ser Leu Phe
        275                 280                 285

Asp Ala Pro Leu His Asn Asn Phe Tyr Thr Ala Ser Lys Ser Ser Gly
    290                 295                 300

Tyr Phe Asp Met Arg Tyr Leu Leu Asn Asn Thr Leu Met Lys Asp Gln
305                 310                 315                 320

Pro Ser Leu Ala Val Thr Leu Val Asp Asn His Asp Thr Gln Pro Gly
                325                 330                 335

Gln Ser Leu Gln Ser Trp Val Glu Pro Trp Phe Lys Pro Leu Ala Tyr
            340                 345                 350

Ala Phe Ile Leu Thr Arg Gln Glu Gly Tyr Pro Cys Val Phe Tyr Gly
        355                 360                 365

Asp Tyr Tyr Gly Ile Pro Lys Tyr Asn Ile Pro Gly Leu Lys Ser Lys
    370                 375                 380

Ile Asp Pro Leu Leu Ile Ala Arg Arg Asp Tyr Ala Tyr Gly Thr Gln
385                 390                 395                 400

Arg Asp Tyr Ile Asp His Gln Asp Ile Ile Gly Trp Thr Arg Glu Gly
                405                 410                 415

Ile Asp Thr Lys Pro Asn Ser Gly Leu Ala Ala Leu Ile Thr Asp Gly
            420                 425                 430

Pro Gly Gly Ser Lys Trp Met Tyr Val Gly Lys Lys His Ala Gly Lys
        435                 440                 445

Val Phe Tyr Asp Leu Thr Gly Asn Arg Ser Asp Thr Val Thr Ile Asn
    450                 455                 460

Ala Asp Gly Trp Gly Glu Phe Lys Val Asn Gly Gly Ser Val Ser Ile
465                 470                 475                 480

Trp Val Ala Lys Thr Ser Asn Val Thr Phe Thr Val Asn Asn Ala Thr
                485                 490                 495

Thr Thr Ser Gly Gln Asn Val Tyr Val Val Ala Asn Ile Pro Glu Leu
            500                 505                 510

Gly Asn Trp Asn Thr Ala Asn Ala Ile Lys Met Asn Pro Ser Ser Tyr
        515                 520                 525

Pro Thr Trp Lys Ala Thr Ile Ala Leu Pro Gln Gly Lys Ala Ile Glu
    530                 535                 540

Phe Lys Phe Ile Lys Lys Asp Gln Ala Gly Asn Val Ile Trp Glu Ser
545                 550                 555                 560

Thr Ser Asn Arg Thr Tyr Thr Val Pro Phe Ser Ser Thr Gly Ser Tyr
                565                 570                 575

Thr Ala Ser Trp Asn Val Pro
            580

<210> SEQ ID NO 4
<211> LENGTH: 4
<212> TYPE: PRT
```

```
<213> ORGANISM: Artificial sequence
<220> FEATURE:
<223> OTHER INFORMATION: Motif
<220> FEATURE:
<221> NAME/KEY: MISC_FEATURE
<222> LOCATION: (2)..(2)
<223> OTHER INFORMATION: Wherein X is R or S
<220> FEATURE:
<221> NAME/KEY: MISC_FEATURE
<222> LOCATION: (3)..(3)
<223> OTHER INFORMATION: Wherein X is A, R, N, D, C, E, Q, G, H, I, L,
      K, M, F, P, S, R, W, Y, or V

<400> SEQUENCE: 4

Phe Xaa Xaa Lys
1

<210> SEQ ID NO 5
<211> LENGTH: 485
<212> TYPE: PRT
<213> ORGANISM: Bacillus halmapalus

<400> SEQUENCE: 5

His His Asn Gly Thr Asn Gly Thr Met Met Gln Tyr Phe Glu Trp His
1               5                   10                  15

Leu Pro Asn Asp Gly Asn His Trp Asn Arg Leu Arg Asp Asp Ala Ser
                20                  25                  30

Asn Leu Arg Asn Arg Gly Ile Thr Ala Ile Trp Ile Pro Pro Ala Trp
            35                  40                  45

Lys Gly Thr Ser Gln Asn Asp Val Gly Tyr Gly Ala Tyr Asp Leu Tyr
50                  55                  60

Asp Leu Gly Glu Phe Asn Gln Lys Gly Thr Val Arg Thr Lys Tyr Gly
65                  70                  75                  80

Thr Arg Ser Gln Leu Glu Ser Ala Ile His Ala Leu Lys Asn Asn Gly
                85                  90                  95

Val Gln Val Tyr Gly Asp Val Val Met Asn His Lys Gly Gly Ala Asp
                100                 105                 110

Ala Thr Glu Asn Val Leu Ala Val Glu Val Asn Pro Asn Asn Arg Asn
            115                 120                 125

Gln Glu Ile Ser Gly Asp Tyr Thr Ile Glu Ala Trp Thr Lys Phe Asp
130                 135                 140

Phe Pro Gly Arg Gly Asn Thr Tyr Ser Asp Phe Lys Trp Arg Trp Tyr
145                 150                 155                 160

His Phe Asp Gly Val Asp Trp Asp Gln Ser Arg Gln Phe Gln Asn Arg
                165                 170                 175

Ile Tyr Lys Phe Arg Gly Asp Gly Lys Ala Trp Asp Trp Glu Val Asp
            180                 185                 190

Ser Glu Asn Gly Asn Tyr Asp Tyr Leu Met Tyr Ala Asp Val Asp Met
        195                 200                 205

Asp His Pro Glu Val Val Asn Glu Leu Arg Arg Trp Gly Glu Trp Tyr
210                 215                 220

Thr Asn Thr Leu Asn Leu Asp Gly Phe Arg Ile Asp Ala Val Lys His
225                 230                 235                 240

Ile Lys Tyr Ser Phe Thr Arg Asp Trp Leu Thr His Val Arg Asn Ala
                245                 250                 255

Thr Gly Lys Glu Met Phe Ala Val Ala Glu Phe Trp Lys Asn Asp Leu
            260                 265                 270

Gly Ala Leu Glu Asn Tyr Leu Asn Lys Thr Asn Trp Asn His Ser Val
        275                 280                 285
```

```
Phe Asp Val Pro Leu His Tyr Asn Leu Tyr Asn Ala Ser Asn Ser Gly
        290                 295                 300

Gly Asn Tyr Asp Met Ala Lys Leu Leu Asn Gly Thr Val Val Gln Lys
305                 310                 315                 320

His Pro Met His Ala Val Thr Phe Val Asp Asn His Asp Ser Gln Pro
                325                 330                 335

Gly Glu Ser Leu Glu Ser Phe Val Gln Glu Trp Phe Lys Pro Leu Ala
            340                 345                 350

Tyr Ala Leu Ile Leu Thr Arg Glu Gln Gly Tyr Pro Ser Val Phe Tyr
        355                 360                 365

Gly Asp Tyr Tyr Gly Ile Pro Thr His Ser Val Pro Ala Met Lys Ala
370                 375                 380

Lys Ile Asp Pro Ile Leu Glu Ala Arg Gln Asn Phe Ala Tyr Gly Thr
385                 390                 395                 400

Gln His Asp Tyr Phe Asp His His Asn Ile Ile Gly Trp Thr Arg Glu
                405                 410                 415

Gly Asn Thr Thr His Pro Asn Ser Gly Leu Ala Thr Ile Met Ser Asp
            420                 425                 430

Gly Pro Gly Gly Glu Lys Trp Met Tyr Val Gly Gln Asn Lys Ala Gly
        435                 440                 445

Gln Val Trp His Asp Ile Thr Gly Asn Lys Pro Gly Thr Val Thr Ile
450                 455                 460

Asn Ala Asp Gly Trp Ala Asn Phe Ser Val Asn Gly Gly Ser Val Ser
465                 470                 475                 480

Ile Trp Val Lys Arg
                485

<210> SEQ ID NO 6
<211> LENGTH: 4
<212> TYPE: PRT
<213> ORGANISM: Artificial Sequence
<220> FEATURE:
<223> OTHER INFORMATION: Amino Acid Motif

<400> SEQUENCE: 6

Phe Thr Gly Lys
1

<210> SEQ ID NO 7
<211> LENGTH: 4
<212> TYPE: PRT
<213> ORGANISM: Artificial Sequence
<220> FEATURE:
<223> OTHER INFORMATION: Amino acid motif

<400> SEQUENCE: 7

Phe Arg Ser Lys
1

<210> SEQ ID NO 8
<211> LENGTH: 4
<212> TYPE: PRT
<213> ORGANISM: Artificial Sequence
<220> FEATURE:
<223> OTHER INFORMATION: Amino acid motif

<400> SEQUENCE: 8

Phe Arg Gly Lys
1
```

```
<210> SEQ ID NO 9
<211> LENGTH: 4
<212> TYPE: PRT
<213> ORGANISM: Artificial Sequence
<220> FEATURE:
<223> OTHER INFORMATION: Amino acid motif

<400> SEQUENCE: 9

Phe Ser Gly Lys
1

<210> SEQ ID NO 10
<211> LENGTH: 4
<212> TYPE: PRT
<213> ORGANISM: Artificial Sequence
<220> FEATURE:
<223> OTHER INFORMATION: Amino acid motif

<400> SEQUENCE: 10

Phe Ser Thr Lys
1

<210> SEQ ID NO 11
<211> LENGTH: 4
<212> TYPE: PRT
<213> ORGANISM: Artificial Sequence
<220> FEATURE:
<223> OTHER INFORMATION: Amino acid motif

<400> SEQUENCE: 11

Phe Arg Cys Lys
1

<210> SEQ ID NO 12
<211> LENGTH: 4
<212> TYPE: PRT
<213> ORGANISM: Artificial Sequence
<220> FEATURE:
<223> OTHER INFORMATION: Amino acid motif

<400> SEQUENCE: 12

Phe Arg Tyr Lys
1

<210> SEQ ID NO 13
<211> LENGTH: 4
<212> TYPE: PRT
<213> ORGANISM: Artificial Sequence
<220> FEATURE:
<223> OTHER INFORMATION: Amino acid motif

<400> SEQUENCE: 13

Phe Ser Ile Lys
1

<210> SEQ ID NO 14
<211> LENGTH: 4
<212> TYPE: PRT
<213> ORGANISM: Artificial Sequence
<220> FEATURE:
<223> OTHER INFORMATION: Amino acid motif

<400> SEQUENCE: 14

Phe Ser Leu Lys
1
```

```
<210> SEQ ID NO 15
<211> LENGTH: 4
<212> TYPE: PRT
<213> ORGANISM: Artificial Sequence
<220> FEATURE:
<223> OTHER INFORMATION: Amino acid motif

<400> SEQUENCE: 15

Phe Arg Leu Lys
1

<210> SEQ ID NO 16
<211> LENGTH: 4
<212> TYPE: PRT
<213> ORGANISM: Artificial Sequence
<220> FEATURE:
<223> OTHER INFORMATION: Amino acid motif

<400> SEQUENCE: 16

Phe Ser Gln Lys
1

<210> SEQ ID NO 17
<211> LENGTH: 4
<212> TYPE: PRT
<213> ORGANISM: Artificial Sequence
<220> FEATURE:
<223> OTHER INFORMATION: Amino acid motif

<400> SEQUENCE: 17

Phe Ser Ser Lys
1

<210> SEQ ID NO 18
<211> LENGTH: 4
<212> TYPE: PRT
<213> ORGANISM: Artificial Sequence
<220> FEATURE:
<223> OTHER INFORMATION: Amino acid motif

<400> SEQUENCE: 18

Phe Arg Asp Lys
1

<210> SEQ ID NO 19
<211> LENGTH: 4
<212> TYPE: PRT
<213> ORGANISM: Artificial Sequence
<220> FEATURE:
<223> OTHER INFORMATION: Amino acid motif

<400> SEQUENCE: 19

Phe Arg Ala Lys
1

<210> SEQ ID NO 20
<211> LENGTH: 4
<212> TYPE: PRT
<213> ORGANISM: Artificial Sequence
<220> FEATURE:
<223> OTHER INFORMATION: Amino acid motif

<400> SEQUENCE: 20

Phe Arg Arg Lys
1

<210> SEQ ID NO 21
```

```
<211> LENGTH: 4
<212> TYPE: PRT
<213> ORGANISM: Artificial Sequence
<220> FEATURE:
<223> OTHER INFORMATION: Amino acid motif

<400> SEQUENCE: 21

Phe Arg Asn Lys
1

<210> SEQ ID NO 22
<211> LENGTH: 4
<212> TYPE: PRT
<213> ORGANISM: Artificial Sequence
<220> FEATURE:
<223> OTHER INFORMATION: Amino acid motif

<400> SEQUENCE: 22

Phe Arg Glu Lys
1

<210> SEQ ID NO 23
<211> LENGTH: 4
<212> TYPE: PRT
<213> ORGANISM: Artificial Sequence
<220> FEATURE:
<223> OTHER INFORMATION: Amino acid motif

<400> SEQUENCE: 23

Phe Arg Gln Lys
1

<210> SEQ ID NO 24
<211> LENGTH: 4
<212> TYPE: PRT
<213> ORGANISM: Artificial Sequence
<220> FEATURE:
<223> OTHER INFORMATION: Amino acid motif

<400> SEQUENCE: 24

Phe Arg His Lys
1

<210> SEQ ID NO 25
<211> LENGTH: 4
<212> TYPE: PRT
<213> ORGANISM: Artificial Sequence
<220> FEATURE:
<223> OTHER INFORMATION: Amino acid motif

<400> SEQUENCE: 25

Phe Arg Ile Lys
1

<210> SEQ ID NO 26
<211> LENGTH: 4
<212> TYPE: PRT
<213> ORGANISM: Artificial Sequence
<220> FEATURE:
<223> OTHER INFORMATION: Amino acid motif

<400> SEQUENCE: 26

Phe Arg Lys Lys
1

<210> SEQ ID NO 27
<211> LENGTH: 4
```

<212> TYPE: PRT
<213> ORGANISM: Artificial Sequence
<220> FEATURE:
<223> OTHER INFORMATION: Amino acid motif

<400> SEQUENCE: 27

Phe Arg Met Lys
1

<210> SEQ ID NO 28
<211> LENGTH: 4
<212> TYPE: PRT
<213> ORGANISM: Artificial Sequence
<220> FEATURE:
<223> OTHER INFORMATION: Amino acid motif

<400> SEQUENCE: 28

Phe Arg Phe Lys
1

<210> SEQ ID NO 29
<211> LENGTH: 4
<212> TYPE: PRT
<213> ORGANISM: Artificial Sequence
<220> FEATURE:
<223> OTHER INFORMATION: Amino acid motif

<400> SEQUENCE: 29

Phe Arg Thr Lys
1

<210> SEQ ID NO 30
<211> LENGTH: 4
<212> TYPE: PRT
<213> ORGANISM: Artificial Sequence
<220> FEATURE:
<223> OTHER INFORMATION: Amino acid motif

<400> SEQUENCE: 30

Phe Arg Trp Lys
1

<210> SEQ ID NO 31
<211> LENGTH: 4
<212> TYPE: PRT
<213> ORGANISM: Artificial Sequence
<220> FEATURE:
<223> OTHER INFORMATION: Amino acid motif

<400> SEQUENCE: 31

Phe Arg Val Lys
1

<210> SEQ ID NO 32
<211> LENGTH: 4
<212> TYPE: PRT
<213> ORGANISM: Artificial Sequence
<220> FEATURE:
<223> OTHER INFORMATION: Amino acid motif

<400> SEQUENCE: 32

Phe Ser Ala Lys
1

<210> SEQ ID NO 33
<211> LENGTH: 4
<212> TYPE: PRT

```
<213> ORGANISM: Artificial Sequence
<220> FEATURE:
<223> OTHER INFORMATION: Amino acid motif

<400> SEQUENCE: 33

Phe Ser Arg Lys
1

<210> SEQ ID NO 34
<211> LENGTH: 4
<212> TYPE: PRT
<213> ORGANISM: Artificial Sequence
<220> FEATURE:
<223> OTHER INFORMATION: Amino acid motif

<400> SEQUENCE: 34

Phe Ser Asn Lys
1

<210> SEQ ID NO 35
<211> LENGTH: 4
<212> TYPE: PRT
<213> ORGANISM: Artificial Sequence
<220> FEATURE:
<223> OTHER INFORMATION: Amino acid motif

<400> SEQUENCE: 35

Phe Ser Glu Lys
1

<210> SEQ ID NO 36
<211> LENGTH: 4
<212> TYPE: PRT
<213> ORGANISM: Artificial Sequence
<220> FEATURE:
<223> OTHER INFORMATION: Amino acid motif

<400> SEQUENCE: 36

Phe Ser Lys Lys
1

<210> SEQ ID NO 37
<211> LENGTH: 4
<212> TYPE: PRT
<213> ORGANISM: Artificial Sequence
<220> FEATURE:
<223> OTHER INFORMATION: Amino acid motif

<400> SEQUENCE: 37

Phe Ser Phe Lys
1

<210> SEQ ID NO 38
<211> LENGTH: 4
<212> TYPE: PRT
<213> ORGANISM: Artificial Sequence
<220> FEATURE:
<223> OTHER INFORMATION: Amino acid motif

<400> SEQUENCE: 38

Phe Ser Pro Lys
1

<210> SEQ ID NO 39
<211> LENGTH: 4
<212> TYPE: PRT
<213> ORGANISM: Artificial Sequence
```

```
<220> FEATURE:
<223> OTHER INFORMATION: Amino acid motif

<400> SEQUENCE: 39

Phe Ser Trp Lys
1

<210> SEQ ID NO 40
<211> LENGTH: 4
<212> TYPE: PRT
<213> ORGANISM: Artificial Sequence
<220> FEATURE:
<223> OTHER INFORMATION: Amino acid motif

<400> SEQUENCE: 40

Phe Ser Tyr Lys
1

<210> SEQ ID NO 41
<211> LENGTH: 4
<212> TYPE: PRT
<213> ORGANISM: Artificial Sequence
<220> FEATURE:
<223> OTHER INFORMATION: Amino acid motif

<400> SEQUENCE: 41

Phe Ser Val Lys
1

<210> SEQ ID NO 42
<211> LENGTH: 4
<212> TYPE: PRT
<213> ORGANISM: Artificial Sequence
<220> FEATURE:
<223> OTHER INFORMATION: Amino acid motif

<400> SEQUENCE: 42

Phe Ser Asp Lys
1

<210> SEQ ID NO 43
<211> LENGTH: 4
<212> TYPE: PRT
<213> ORGANISM: Artificial Sequence
<220> FEATURE:
<223> OTHER INFORMATION: Amino acid motif

<400> SEQUENCE: 43

Phe Ser Met Lys
1
```